US011866683B2

(12) United States Patent
Martin et al.

(10) Patent No.: US 11,866,683 B2
(45) Date of Patent: Jan. 9, 2024

(54) CELL CULTURE APPARATUSES WITH MANIFOLDS INCLUDING COLUMN STRUCTURES

(71) Applicant: CORNING INCORPORATED, Corning, NY (US)

(72) Inventors: Gregory Roger Martin, Acton, ME (US); Allison Jean Tanner, Portsmouth, NH (US)

(73) Assignee: CORNING INCORPORATED, Corning, NY (US)

( * ) Notice: Subject to any disclaimer, the term of this patent is extended or adjusted under 35 U.S.C. 154(b) by 0 days.

(21) Appl. No.: 16/758,066

(22) PCT Filed: Nov. 5, 2018

(86) PCT No.: PCT/US2018/059180
§ 371 (c)(1),
(2) Date: Apr. 22, 2020

(87) PCT Pub. No.: WO2019/090211
PCT Pub. Date: May 9, 2019

(65) Prior Publication Data
US 2021/0189314 A1    Jun. 24, 2021

Related U.S. Application Data

(60) Provisional application No. 62/582,086, filed on Nov. 6, 2017.

(51) Int. Cl.
*C12M 1/00* (2006.01)
*C12M 3/00* (2006.01)
*C12M 1/12* (2006.01)

(52) U.S. Cl.
CPC ............ *C12M 23/40* (2013.01); *C12M 23/44* (2013.01); *C12M 23/58* (2013.01); *C12M 29/20* (2013.01); *C12M 37/04* (2013.01)

(58) Field of Classification Search
CPC ...... C12M 23/40; C12M 23/44; C12M 23/58; C12M 29/20; C12M 37/04
(Continued)

(56) References Cited

U.S. PATENT DOCUMENTS 5,240,854 A    8/1993  Berry et al.
7,745,209 B2   6/2010  Martin et al.
(Continued)

FOREIGN PATENT DOCUMENTS

JP    2010-512148 A    4/2010
JP    2011-528226 A    11/2011
(Continued)

OTHER PUBLICATIONS

International Search Report and Written Opinion of the International Searching Authority; PCT/US2018/059180; dated Feb. 4, 2019; 10 Pages; European Patent Office.
(Continued)

*Primary Examiner* — Michael L Hobbs
*Assistant Examiner* — Lenora A Abel
(74) *Attorney, Agent, or Firm* — Chandra J. Duncan

(57) ABSTRACT

A cell culture apparatus includes a cell culture module including multiple cell culture chambers. A manifold connects the multiple cell culture chambers together along a side of the cell culture module. The manifold includes a side wall base structure connected to the side of the cell culture module and a column structure that is formed as a monolithic part of the side wall base structure. The column structure defines a fluid flow pathway through the manifold and to inlets to the cell culture chambers to allow filling and emptying of the cell culture chambers of liquid medium.

9 Claims, 18 Drawing Sheets

(58) Field of Classification Search
USPC .......................................................... 435/294.1
See application file for complete search history.

(56) References Cited

U.S. PATENT DOCUMENTS

| | | |
|---|---|---|
| 7,820,431 B2 | 10/2010 | Kenney et al. |
| 7,897,379 B2 | 3/2011 | Kenney et al. |
| 8,178,345 B2 | 5/2012 | Bennett et al. |
| 8,187,868 B2 | 5/2012 | Kenney et al. |
| 8,273,572 B2 | 9/2012 | Martin et al. |
| 8,809,044 B2 * | 8/2014 | Wilson .................. C12M 23/34 435/297.5 |
| 9,045,721 B2 | 6/2015 | Martin et al. |
| 9,290,730 B2 | 3/2016 | Martin et al. |
| 2008/0176318 A1 | 7/2008 | Wilson et al. |
| 2010/0216229 A1 * | 8/2010 | Kenney .................. C12M 23/34 435/303.1 |
| 2016/0115434 A1 | 4/2016 | Pankratz et al. |
| 2016/0137961 A2 | 5/2016 | Clark et al. |

FOREIGN PATENT DOCUMENTS

| | | |
|---|---|---|
| JP | 2012-518436 A | 8/2012 |
| JP | 2013-540444 A | 11/2013 |

OTHER PUBLICATIONS

Japanese Patent Application No. 2020-524766, Office Action dated Oct. 18, 2022, 4 pages (English translation only), Japanese Patent Office.

* cited by examiner

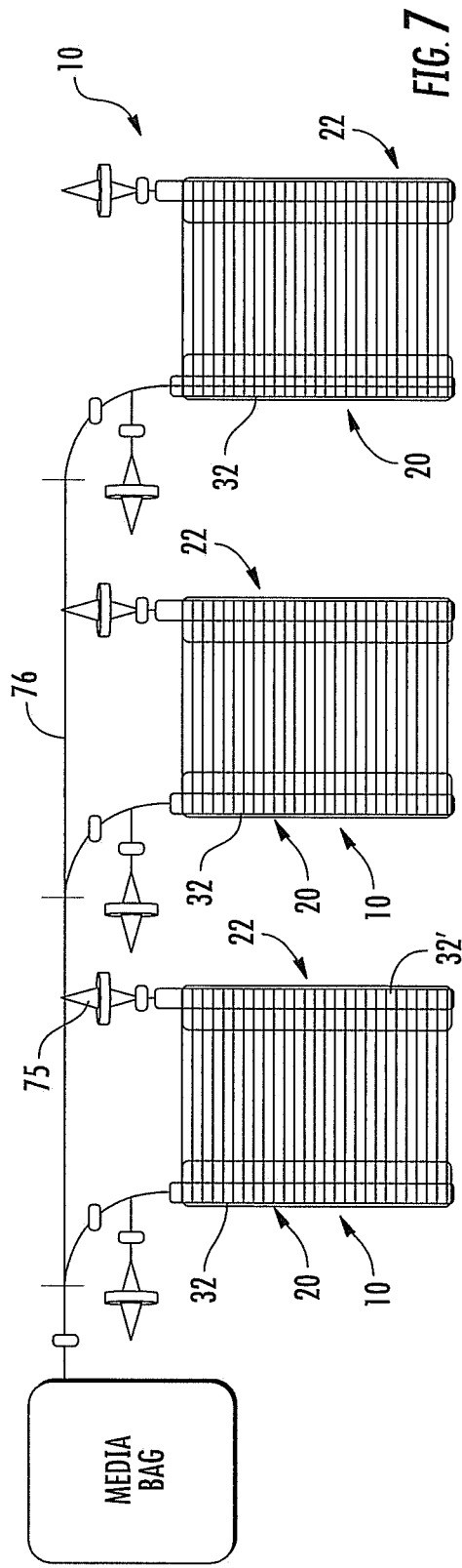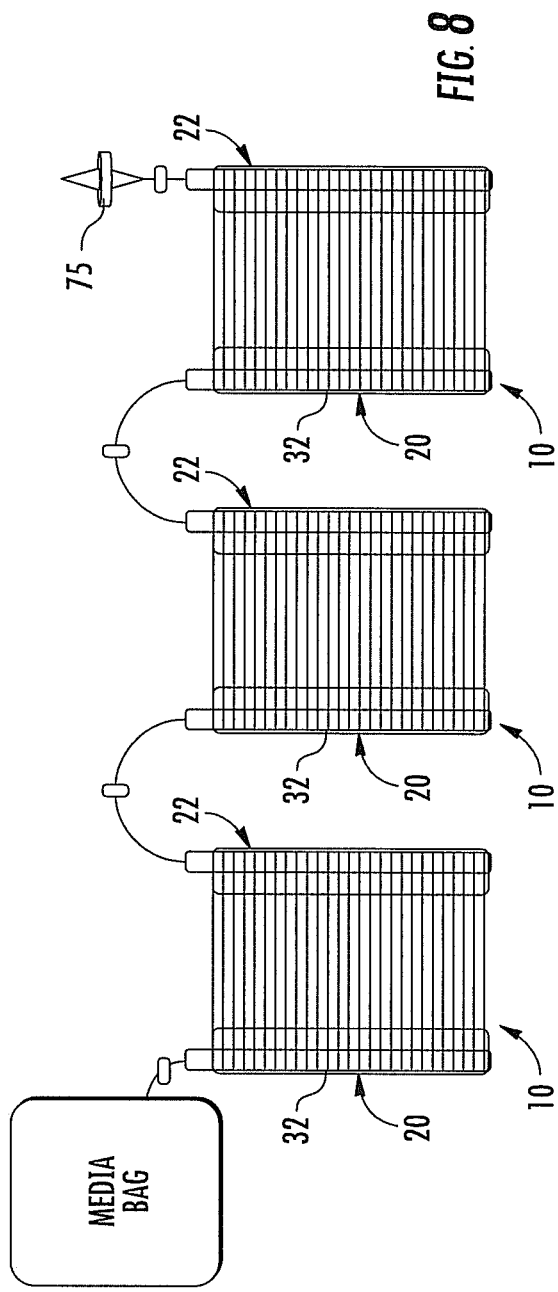
FIG. 7
FIG. 8

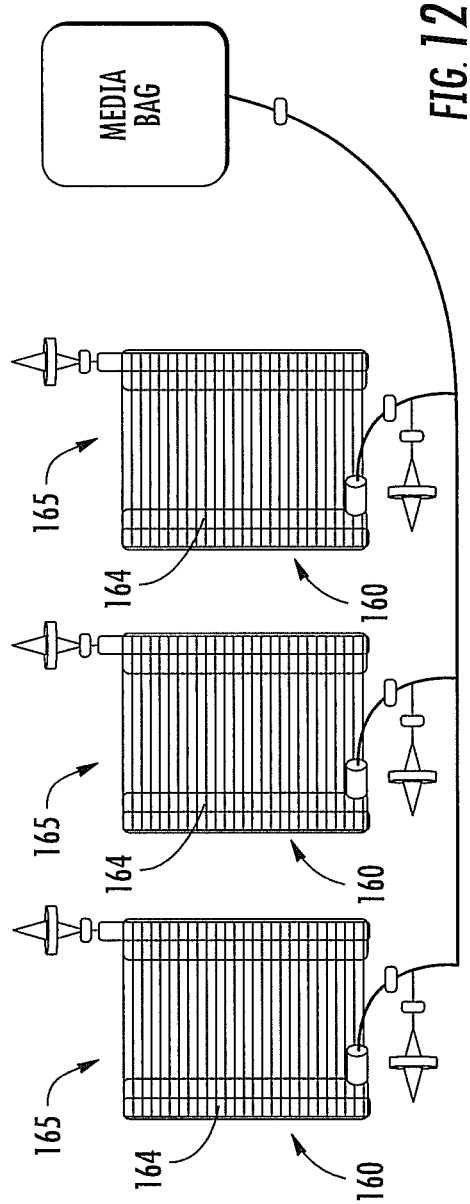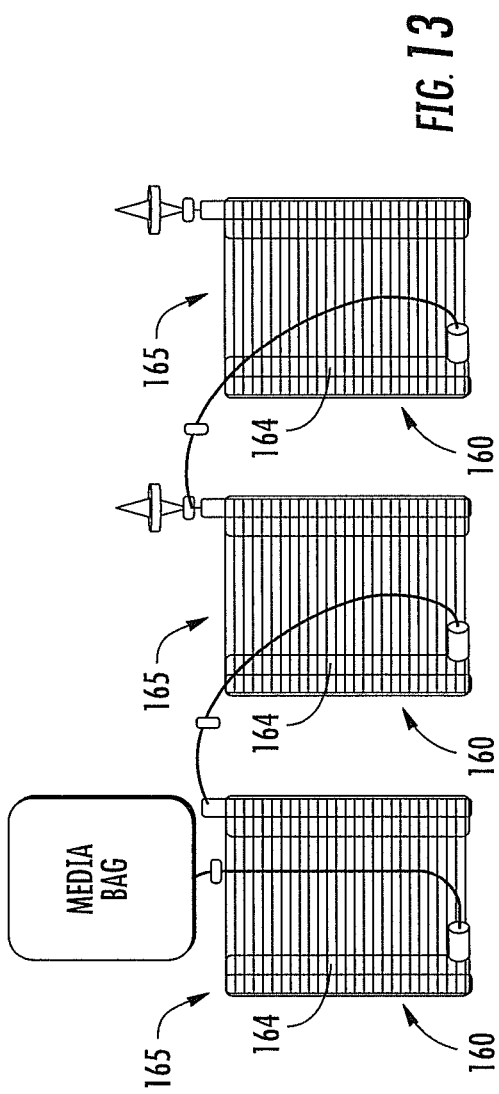

CELL CULTURE APPARATUSES WITH MANIFOLDS INCLUDING COLUMN STRUCTURES

CROSS-REFERENCE

This is a national stage application under 35 U.S.C. § 371 of International Application No. PCT/US2018/059180 filed on Nov. 5, 2018, which claims the benefit of and priority to U.S. Provisional Application No. 62/582,086, titled "Cell Culture Apparatuses with Manifolds Including Column Structures," filed Nov. 6, 2017, the details of which are incorporated herein by reference in their entirety.

FIELD

The present disclosure relates to apparatuses for culturing cells and, in particular, cell culture apparatuses with manifolds including column structures.

BACKGROUND

Many types of cell culture articles are constructed to provide stacked or stackable units for culturing cells. For example, T-flasks are typically made to have flat top and bottom surfaces that allow T-flasks to be stacked, providing space savings. Some modified T-flasks have multiple parallel culture surfaces within the flask to reduce time and effort associated with filling and emptying. Other culture apparatuses are multi-component assemblies having a plurality of parallel or stacked culture surfaces. Manipulating stacked cell culture devices can be challenging. These devices must be filled, usually on their sides, and then turned so that the cell culture surfaces are horizontal. It can be challenging to fill and manipulate these large devices, which can be heavy when filled with liquid. In addition, it is important to maintain the integrity and sterility of these devices.

An exemplary cell culture article is Corning's HYPERStack™ system. The HYPERStack™ system includes multiple modules formed of individual stackette layers that can be interconnected by flexible tubes that connect to tube connectors. The modules are interconnected for filling and emptying the HYPERStack™ system. Valves and other devices may be used to control fluid flow into and out of the HYPERStack™ system. The use of these valves and other devices can be cumbersome and provide potential leak locations. There is a need for improved cell culture articles with increased capacity and improved flow control features. In addition, it is desirable to reduce the risk of leaks and contamination, minimize wasteful use of expensive media and valuable cells, in cell culture articles that are easier to maneuver, fill and empty.

BRIEF SUMMARY

In a first aspect, a cell culture apparatus, comprises: a cell culture module comprising multiple cell culture chambers; and a manifold that connects the multiple cell culture chambers together along a side of the cell culture module, the manifold comprising a side wall base structure connected to the side of the cell culture module and a column structure that is formed as a monolithic part of the side wall base structure, the column structure defining a fluid flow pathway through the manifold and to inlets to the cell culture chambers to allow filling and emptying of the cell culture chambers of liquid medium.

According to a second aspect, there is provided the cell culture apparatus of aspect 1, wherein the cell culture apparatus comprises multiple cell culture modules, the manifold comprises manifold segments, each manifold segment is associated with one of the cell culture modules.

According to a third aspect, there is provided the cell culture apparatus of aspect 2, wherein each manifold segment comprises a side wall base structure segment and a column structure segment that is formed as a monolithic part of the side wall base structure segment.

According to a fourth aspect, there is provided the cell culture apparatus of aspect 3, wherein the column structure segments of adjacent manifold segments are interconnected and in fluid communication.

According to a fifth aspect, there is provided the cell culture apparatus of aspect 4, wherein the column structure segments of adjacent manifold segments are interconnected by a sealing ring.

According to a sixth aspect, there is provided the cell culture apparatus of aspect 5, wherein the sealing ring seals an interface between the column structure segments of adjacent manifold segments.

According to a seventh aspect, there is provided the cell culture apparatus of aspect 5 or 6, wherein the sealing ring comprises relatively thick portions that are separated by a relatively thin portion in the form of a notch that defines an area of increased flexibility compared to the thick portions.

According to an eighth aspect, there is provided the cell culture apparatus of any of aspects 5-7, wherein each column structure segment comprises a shroud structure, wherein adjacent shroud structures face each other thereby forming a partial enclosure that extends about an entire periphery of the sealing ring.

In a ninth aspect, A method of forming a cell culture apparatus, the method comprising: stacking one cell culture module on another cell culture module, the cell culture modules comprising multiple cell culture chambers; and connecting the cell culture chambers using a manifold, the manifold comprising a side wall base structure and a column structure that is formed as a monolithic part of the side wall base structure, the column structure defining a fluid flow pathway through the manifold and to the cell culture chambers to allow filling and emptying of the cell culture chambers of liquid medium.

According to a tenth aspect, there is provided the method of aspect 9, wherein the manifold comprises manifold segments, the method comprising connecting each manifold segment to one of the cell culture modules.

In an eleventh aspect, there is provided the method of aspect 10, wherein each manifold segment comprises a side wall base structure segment and a column structure segment that is formed as a monolithic part of the side wall base structure segment.

In a twelfth aspect, there is provided the method of aspect 11 comprising connecting the column structure segments of adjacent manifold segments such that the column segments of the adjacent manifold segments are in fluid communication.

In a thirteenth aspect, there is provided the method of aspect 12 comprising connecting the column structure segments of adjacent manifold segments by a sealing ring.

In a fourteenth aspect, there is provided the method of aspect 13, wherein sealing an interface between the column structure segments of adjacent manifold segments using the sealing ring.

In a fifteenth aspect, there is provided the method of aspect 13 or 14, wherein the sealing ring comprises relatively thick portions that are separated by a relatively thin portion in the form of a notch that defines an area of increased flexibility compared to the thick portions.

In a sixteenth aspect, there is provided the aspect of any of aspects 13-15, wherein each column structure segment comprises a shroud structure, wherein adjacent shroud structures face each other thereby forming a partial enclosure that extends about an entire periphery of the sealing ring.

In a seventeenth aspect, a cell culture apparatus, comprises: at least two cell culture modules, each cell culture module comprising at least two cell culture chambers; and a manifold that connects the at least two cell culture manifolds together, the manifold comprising multiple manifold segments, each manifold segment comprising a side wall base structure segment and a column structure segment that is formed as a monolithic part of the side wall base structure segment, the column structure segments connected together and defining a fluid flow pathway through the manifold and to the cell culture chambers to allow filling and emptying of the cell culture chambers of liquid medium.

In an eighteenth aspect, there is provided the cell culture apparatus of aspect 17, wherein the column structure segments of adjacent manifold segments are interconnected by a sealing ring.

In a nineteenth aspect, there is provided the cell culture apparatus of aspect 18, wherein the sealing ring seals an interface between the column structure segments of adjacent manifold segments.

In a twentieth aspect, there is provided the cell culture apparatus of aspect 18, wherein each column structure segment comprises a shroud structure, wherein adjacent shroud structures face each other thereby forming a partial enclosure that extends about an entire periphery of the sealing ring.

In a twenty-first aspect, a cell culture apparatus, comprises: a cell culture modules comprising multiple cell culture chambers; a fluid manifold that connects the cell culture chambers together, the fluid manifold comprising a side wall base structure and a column structure, the column structure defining a fluid flow pathway to allow filling and emptying of the cell culture chambers; and an air manifold that connects the at least two cell culture manifolds together, the air manifold comprising a side wall base structure and a column structure, the column structure of the air manifold defining a fluid flow pathway to allow filling and emptying of the cell culture chambers; wherein the column structure of the air manifold comprises one or more indent structure that provides the column structure of the air manifold with a necked-down region.

According to a twenty-second aspect, there is provided the cell culture apparatus of aspect 21, wherein the air manifold comprises manifold segments, each manifold segment is associated with one of the at least two cell culture modules and each manifold segment comprises a side wall base structure segment and a column structure segment that is formed as a monolithic part of the side wall base structure segment.

According to a twenty-third aspect, there is provided the cell culture apparatus of aspect 22, wherein each column structure segment comprises an indent structure.

According to a twenty-fourth aspect, there is provided the cell culture apparatus of any of aspects 21-23, further comprising a riser having an internal volume that is located between the column structure of the air manifold and an air outlet tube of the column structure of the air manifold.

According to a twenty-fifth aspect, there is provided the cell culture apparatus of any of aspects 21-24, further comprising an air outlet tube that is in fluid communication with the column structure of the air manifold, the air outlet tube having a central axis that is offset laterally from a central axis of the column structure of the air manifold.

In an additional aspect, there is provided a cell culture apparatus, comprising a cell culture module comprising multiple cell culture chambers; each cell culture chamber having a top, a bottom and sidewalls, defining an interior space for culturing cells; wherein each cell culture chamber comprises at least one inlet in a sidewall of the cell culture chamber through which liquid can flow into and out of the cell culture chamber; wherein the multiple cell culture chambers are stacked one above the other to form the cell culture module; a manifold comprising a side wall base structure and a column; wherein the manifold is aligned along a side of the cell culture module; wherein the manifold provides a fluid pathway from a manifold opening to each of the cell culture chambers through cell culture inlets; wherein the manifold opening extends above the top-most stacked cell culture chamber; and wherein the column provides an enlarged volume inside the manifold to enable fluid to flow through the manifold to the cell culture chamber inlets.

Culture apparatuses described herein may be stacked into multi-layer culture chamber assemblies where individual chambers or groups of chambers are connected to each other via one or more manifolds. The manifolds include column structures that are formed as a monolithic part of the manifolds. The column structures may allow for use of the culture apparatuses as closed or open systems and may facilitate filling and/or emptying the culture apparatuses without any need for turning or repositioning the culture assemblies only during the filling and/or emptying processes. This and other advantages will be readily understood from the following detailed descriptions when read in conjunction with the accompanying drawings.

BRIEF DESCRIPTION OF THE DRAWINGS

FIG. 7 illustrates a filling operation where multiple cell culture apparatuses are filled in parallel, according to one or more embodiments shown and described herein;

FIG. 8 illustrates another filling operation where multiple cell culture apparatuses are filled is series, according to one or more embodiments shown and described herein;

FIG. 12 illustrates a filling operation where multiple cell culture apparatuses are filled in parallel, according to one or more embodiments shown and described herein;

FIG. 13 illustrates another filling operation where multiple cell culture apparatuses are filled is series, according to one or more embodiments shown and described herein;

Figure 1:
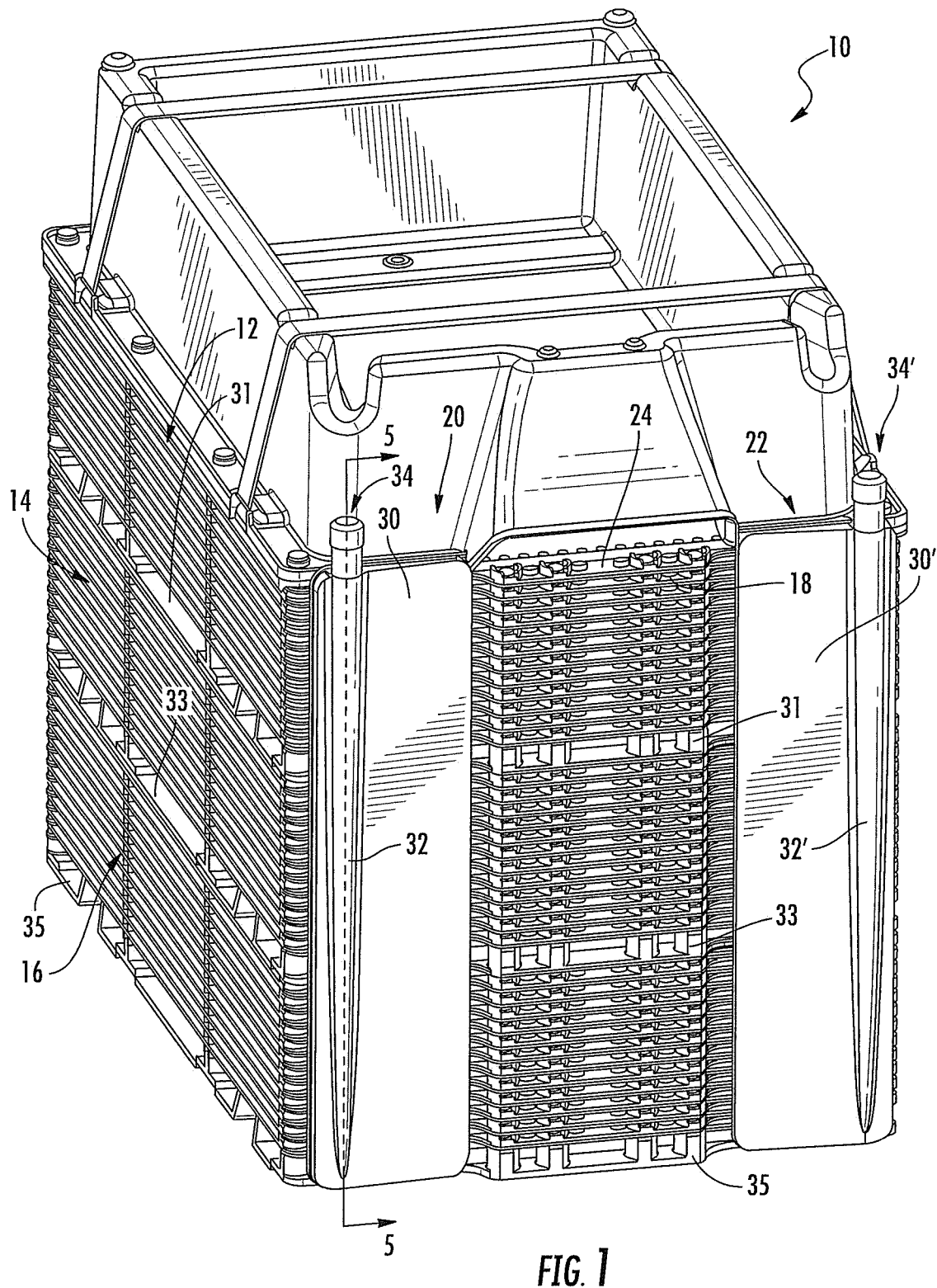
FIG. 1 is a perspective view of a cell culture apparatus including manifolds, according to one or more embodiments shown and described herein.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified.

The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to".

The present disclosure describes, inter alia, cell culture modules include a plurality of growth or culture surfaces in cell culture chambers coupled together via manifolds to form the cell culture modules. The cell culture modules can be further coupled to additional cell culture modules via manifolds to form stacked cell culture apparatuses. The plurality of culture surfaces may be stacked in a multi-layer configuration. The manifold includes an integral column structure that is formed as a monolithic part of the manifold. The column structure includes an inlet port and provides at least part of a fluid flow pathway from the inlet port that is in fluid communication with the individual cell culture chambers within the cell culture modules. The manifold may be configured to allow filling of the individual or groups of the cell culture chambers from the top down, bottom up and/or simultaneously depending, at least in part, on the manifold and column structure configuration. The manifolds and associated column structures may provide a closed system where the column structures can be connected to flexible tubing to isolate the cell culture chambers from the environment during use of the cell culture apparatuses. In other embodiments, the manifolds and associated column structures may provide an open system where fluids can be poured from the environment directly into the column structures (e.g., by removing a cap).

Nearly any cell culture article having a plurality of stacked layers or that can be stacked to form layers can be adapted to include a manifold as described herein. Examples of such cell culture articles include T-flasks, TRIPLE-FLASK cell culture vessels (Nunc., Intl.), HYPERFlask™ cell culture vessels (Corning, Inc.), CellSTACK™ culture chambers (Corning, Inc.), CellCube® modules (Corning, Inc.), CELL FACTORY culture apparatuses (Nunc, Intl.), HYPERStack™ and cell culture articles as described in U.S. Pat. No. 9,752,111, titled Cell Culture System with Manifold.

Referring to FIG. 1, a cell culture apparatus 10 includes three cell culture modules 12, 14 and 16, each containing multiple cell culture chambers 18, which are stacked, one on top of the other, to form the multiple layer cell culture apparatus 10. Each cell culture chamber 18 is an individual cell culture layer having a top, a bottom and sidewalls which define an interior space for culturing cells. In embodiments, the top, bottom, sidewalls, or a combination of these may be gas permeable. In embodiments, there is an inlet in the sidewall of each cell culture chamber adjacent to or coupled to a manifold 20 and 22 to allow fluid to flow from the manifold 20 or 22 into each cell culture chamber 18. Each cell culture module 12, 14 and 16 utilizes two manifolds 20 and 22. Liquid may enter and exit the cell culture chambers of modules 12, 14 and 16 through the first manifold 20. Thus, the first manifold 20 may be referred to as a fluid manifold. Air may enter and exit the cell culture modules 12, 14 and 16 through the second manifold 22. Thus, the second manifold 22 may be referred to as an air manifold.

As shown in FIG. 1, the inlet, which may be a barbed inlet 34, extends above the top-most stackette or cell culture chamber 18 when the device is arranged in cell culture configuration—so that the cell culture chambers 18 are horizontal.

Figure 2:
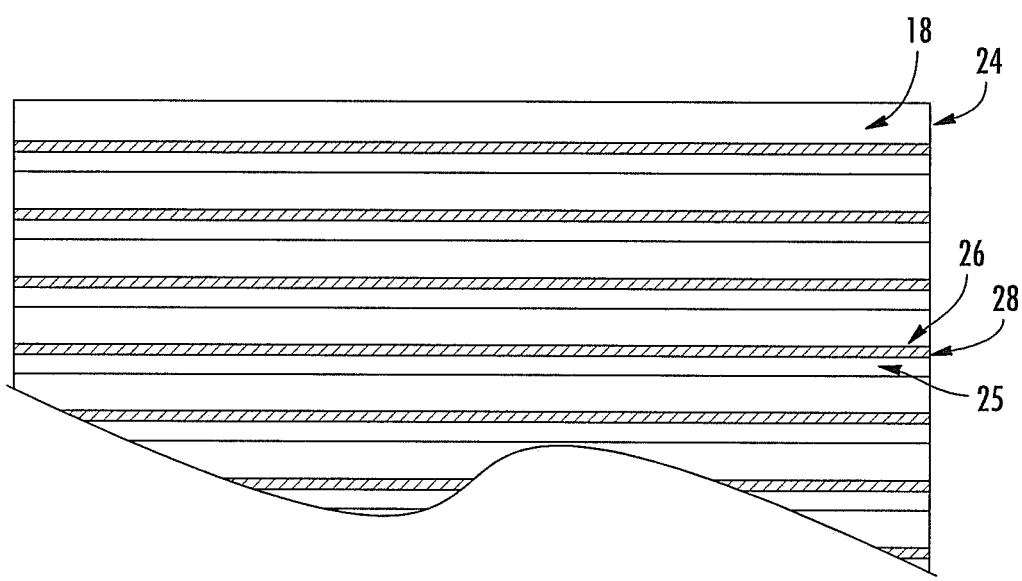
FIG. 2 is a schematic view of a stack of stackette layers for use with the cell culture apparatus of FIG. 1, according to one or more embodiments shown and described herein.

The configuration of cell culture chambers 18 is shown in FIG. 2. The cell culture modules 12, 14 and 16 may each include multiple stackette layers, 24, also called cell culture chambers 18 that, when stacked together, form the multiple cell culture chambers 18 having tracheal spaces (air spaces) 25 therebetween. FIG. 2 is a schematic representation of the multiple stackette layers 24 that are stacked together to form the layered cell culture chambers 18. The cell culture chambers 18 may each be defined by a generally transparent bottom cell culture surface 26 and a generally transparent top surface 29 and also by sidewalls (not shown). The cell culture surfaces 26 are adjacent to tracheal spaces 25. The cell culture surfaces 26 may include a gas permeable, liquid impermeable film 28. This allows for the transfer of gasses between the cell culture chambers 18 and the tracheal spaces 25 which are in gas communication with the exterior of the cell culture apparatus 10, through the gas permeable, liquid impermeable film 28. When cells are cultured in the cell culture chambers 18, they fall by gravity onto the cell culture surfaces 26 where they are bathed by cell culture media in the cell culture chambers 18, and they are able to access oxygen through the gas permeable, liquid impermeable film 28 upon which they reside. Referring back to FIG. 1, the cell culture modules 12, 14 and 16 may be separated from one another by spacers 31, 33 and 35. The spacers 31, 33 and 35 can provide structural support for the individual cell culture modules 12, 14 and 16. In some embodiments, spacers 31 and/or 33 may be replaced by additional stackette layers 24 to provide a higher total number of cell culture chambers 18. Stackettes 24 which define cell culture chambers 18, are stacked together to form modules 12, 14 and 16. Further, a riser volume may be provided above the cell culture module 12 to catch residual air, rather than air residing in the cell culture chambers 18.

A cell culture module, or portions thereof, as described herein may be formed from any suitable material. Preferably, materials intended to contact cells or culture media are compatible with the cells and the media. Typically, cell culture modules are formed from polymeric material. Examples of suitable polymeric materials include polystyrene, polymethylmethacrylate, polyvinyl chloride, polycarbonate, polysulfone, polystyrene copolymers, fluoropolymers, polyesters, polyamides, polystyrene butadiene copolymers, fully hydrogenated styrenic polymers, polycarbonate PDMS copolymers, and polyolefins such as polyethylene, polypropylene, polymethyl pentene, polypropylene copolymers and cyclic olefin copolymers, and the like.

In some embodiments, the culture units contain the gas permeable, liquid impermeable film 28 to allow transfer of gasses between the cell culture chamber 18 and ultimately with the exterior of the cell culture assembly. Such culture units can include spacers or spacer layers positioned adjacent the film, exterior to the chamber, to allow air flow between stacked units. One commercially available example of a cell culture apparatus containing such stacked gas permeable culture units is Corning's HYPERStack™ cell culture apparatus. Examples of suitable gas permeable polymeric materials useful for forming a film include polystyrene, polyethylene, polycarbonate, polyolefin, ethylene vinyl acetate, polymethylpentene, polypropylene, polytetrafluoroethylene (PTFE), or compatible fluoropolymer, a silicone rubber or copolymer, poly(styrene-butadiene-styrene) or combinations of these materials. As manufacturing and compatibility for the growth of cells permits, various polymeric materials may be utilized. Preferably the film is of a thickness that allows for efficient transfer of gas across the film. For example, a polystyrene film may be of a thickness of about 0.003 inches (about 75 micrometers), though various thicknesses are also permissive of cell growth. As such, the film may be of any thickness, preferably between about 25 and 250 micrometers, or between approximately 25 and 125 micrometers. The film allows for the free exchange of gases between the chamber of the assembly and the external environment and may take any size or shape. Preferably, the film is durable for manufacture, handling, and manipulation of the apparatus.

As mentioned above with reference to FIG. 1, the cell culture modules 12, 14 and 16 and their individual cell culture chambers 18 may be connected together using the manifolds 20 and 22. That is, manifolds 20 and 22 provide a fluid pathway to introduce media and cells into the manifold, and into individual cell culture chambers 18. The manifold 20 includes a side wall base structure 30 and a column structure 32 that is formed as a monolithic part of the side wall base structure 30 providing a unitary manifold 20. The column structure provides an enlarged volume inside the manifold to enable fluid to flow through the manifold to the cell culture chambers 18. Manifold includes a manifold opening, shown in FIG. 1 as a barb structure 34. In embodiments, the manifold opening extends above the top-most stacked cell culture chamber 18, when the apparatus is arranged in cell culture orientation. The column structure 32 includes a barb structure 34 and provides at least part of a fluid flow pathway from the barb structure 34 to the individual cell culture chambers 18 within the cell culture modules 12, 14 and 16. The manifold 20 may be configured to allow filling and emptying of the cell culture chambers 18 through, for example, ports 52 (as shown in FIG. 2). The column structure 32 provides an enlarged volume to allow for faster and more efficient filling and emptying of the cell culture chambers 18.

The manifold 22 also includes a side wall base structure 30' and a column structure 32' that is formed as a monolithic part of the side wall base structure 30' providing a unitary manifold 22. The column structure 32' includes a barb structure 34' and provides at least part of a fluid flow pathway from the individual cell culture chambers 18 within the cell culture modules 12, 14 and 16 to the barb structure 34'. The manifold 22 may be configured to allow filling and emptying of the cell culture chambers 18 by allowing air to enter and exit the cell culture apparatus 10.

Figure 3D:
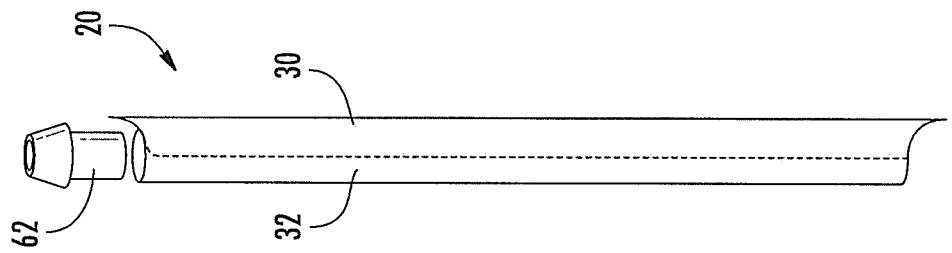
FIG. 3D is a side schematic view of the manifold including column structure of FIG. 3c.
Figure 3C:
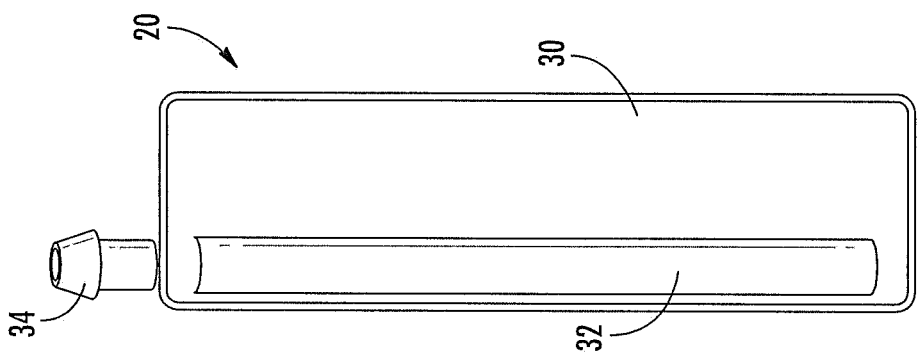
FIG. 3C is a schematic view of a manifold including a column structure for use with the cell culture apparatus of FIG. 1, according to one or more embodiments shown and described herein.
Figure 3B:
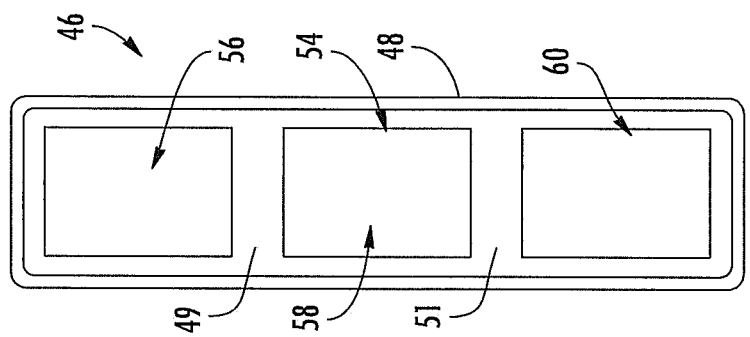
FIG. 3B is a schematic view of a unitary manifold adapter for use with the cell culture apparatus of FIG. 1, according to one or more embodiments shown and described herein.
Figure 3A:
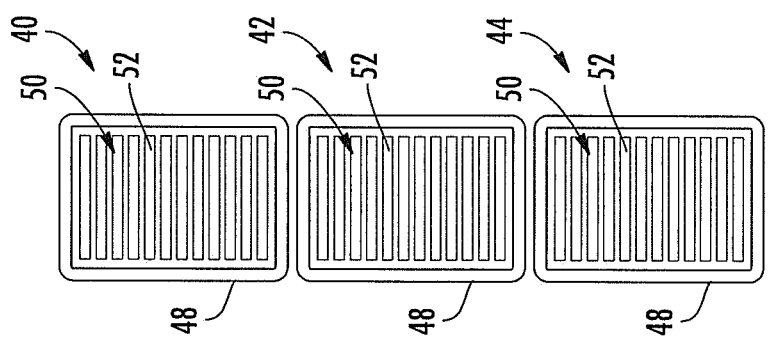
FIG. 3A is a schematic view of multiple module adapters for use with the cell culture apparatus of FIG. 1, according to one or more embodiments shown and described herein.

Referring to FIGS. 3A-3C, an exploded, schematic view of an optional manifold assembly 36 including the manifold 20 is illustrated. Referring first to FIG. 3A, a front view of module adapters 40, 42 and 44 are illustrated. The module adapters 40, 42 and 44 are formed of a suitable material that is used to seal against each of the cell culture modules 12, 14 and 16 individually and to provide a seal between the cell culture chambers 18 and a unitary manifold adapter 46. As can be seen, the module adapters 40, 42 and 44 each include a perimeter 48 that seals to the manifold adapter 46. The module adapters 40, 42 and 44 also include a module adapter body 50 with multiple ports 52 that each provides ingress and egress to the individual cell culture chambers 18. In embodiments, when an apparatus having three modules is assembled, these module adapters may be affixed to the modules to allow for efficient connections between the manifold 20 and the modules 48.

FIG. 3B illustrates an optional unitary manifold adapter 46. The unitary manifold adapter 46 is formed of a suitable material that is used to seal between all of the module adapters 40, 42 and 44 and the side wall base structure 30 of the manifold 20. The unitary manifold adapter 46 includes a perimeter 48 and intermediate portions 49 and 51 that seal to the side base wall of the manifold 20. The unitary manifold adapter 46 also include a unitary manifold adapter body 54 that seals to the perimeters 48 of the module adapters 40, 42 and 44, thereby defining module openings 56, 58 and 60. Each module opening 56 58 and 60 is sized to expose the ports 52 of the module adapters 40, 42 and 44 to the fluid flow path between the manifold 20 and the cell culture chambers 18.

Referring to FIG. 3C, the manifold 20 is illustrated and includes the side wall base structure 30 and the column structure 32 that is formed as a monolithic part of the side wall base structure 30 providing the unitary manifold. The side wall base structure 30 seals against the unitary manifold adapter 46 thereby forming a fluid-tight seal between the manifold 20 and the cell culture modules 12, 14 and 16. In some embodiments, the column structure 32 may include the barb structure 34 that can facilitate connection with a tube for a filling or emptying operation in a closed system. The barb structure may be a component separate from the column structure 32, or may be monolithic with the column structure 32. If the barb structure 34 is a separate component, any suitable method of attaching the barb structure 34 to the column structure 32 may be used, such as adhesive, thermal bonding, ultrasonic welding, infrared welding, laser welding, etc. Separately forming the barb structure 34 can allow for increased access to the cell culture apparatus 10 during assembly. Forming the barb structure 34 monolithic with the column structure 32 can eliminate a step of attaching the barb structure 34 to the column structure 32. FIG. 3D illustrates a side view of the manifold 20.

Figure 4:
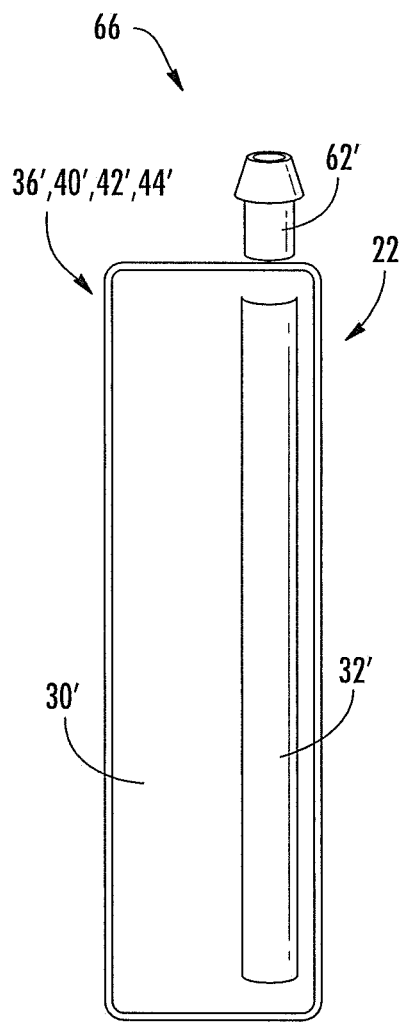
FIG. 4 is a schematic view of another manifold for use with the cell culture; apparatus of FIG. 1, according to one or more embodiments shown and described herein.

Referring briefly to FIG. 4, the manifold 22 and associated manifold assembly 66 may include the same features as the manifold assembly 36 of FIGS. 3A-3C. The side wall base structure 30' seals against a unitary manifold adapter 36' and module adapters 40', 42' and 44' thereby forming a fluid-tight seal between the manifold 22 and the cell culture modules 12, 14 and 16.

Figure 5:
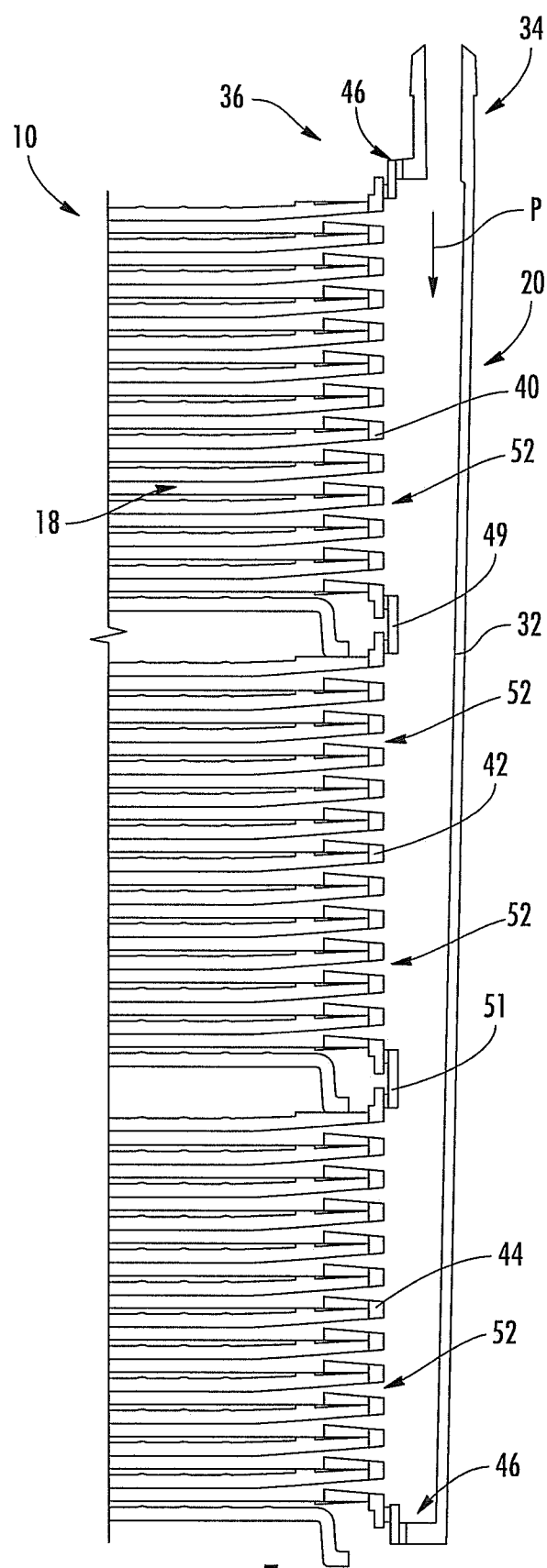
FIG. 5 is a section view along lines 5-5 of the cell culture apparatus of FIG. 1, according to one or more embodiments shown and described herein.

Referring to FIG. 5, a section view of the cell culture apparatus 10 and manifold assembly 36 are illustrated through line 5-5 of FIG. 1. The manifold assembly 36 includes the manifold 20 that includes the column structure 32. The column structure 32 provides the fluid flow path P that extends between the manifold 20 and the module adapters 40, 42 and 44 and leads to the cell culture chambers 18 that are stacked one over the other, via the ports 52. In particular, the unitary manifold adapter 46 is located behind the manifold 20 and seals between the manifold 20 and the module adapters 40, 42 and 44. In some embodiments, an adhesive or other sealant material 68 may be used between the manifold 20, unitary manifold adapter 36 and module adapters 40, 42 and 44. Thus, the fluid flow path P extends from the barb structure 34, through the column structure 32 and into the cell culture chambers 18 through the ports 52 that provide ingress and egress to the cell culture chambers 18. The column structure 32 provides an enlarged volume to improve fluid flow into and out of the cell culture chambers 18, which improves the speed at which the device can be filled and emptied.

The components can be joined by any suitable method including adhesive, thermal bonding, ultrasonic welding, infrared welding, laser welding, etc. To accommodate laser welding, a black color may be compounded into a shot of polymer that extends about a periphery of each adapter.

Figure 6:
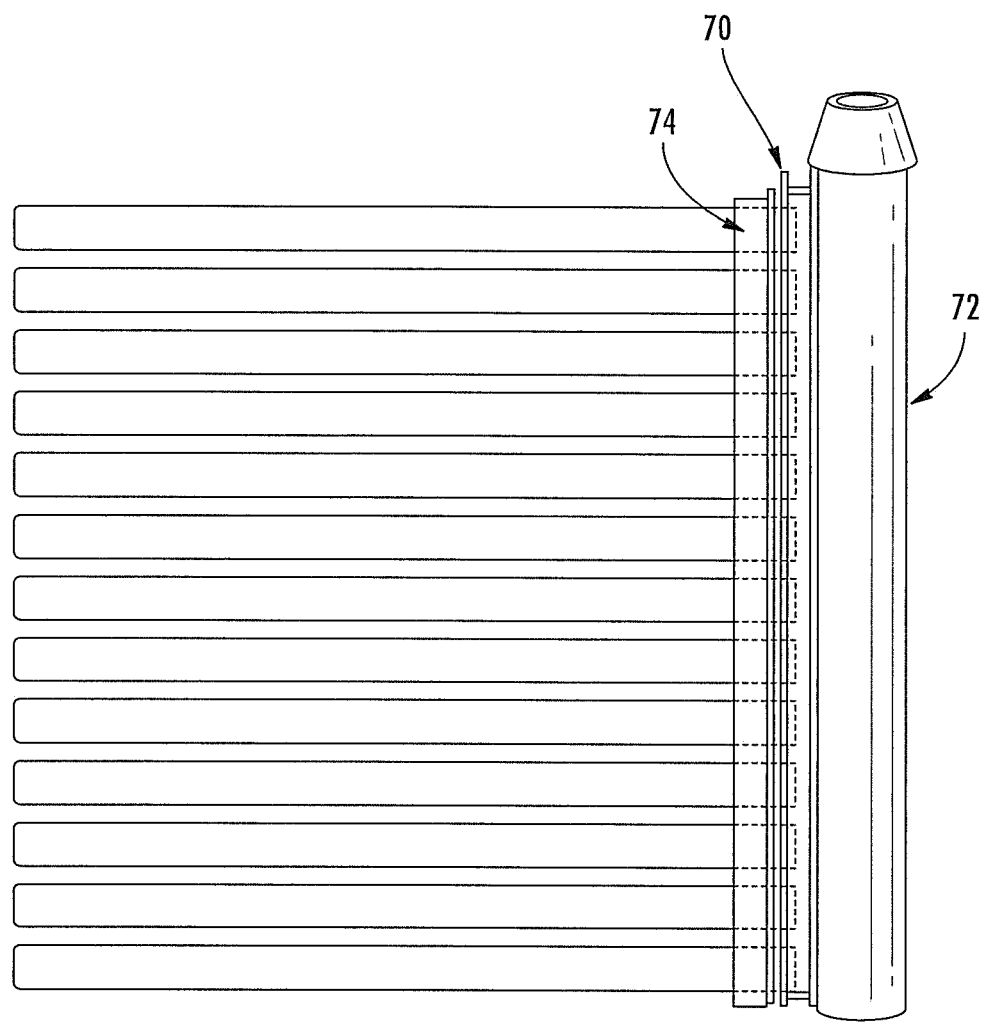
FIG. 6 is a schematic view of another embodiment of a cell culture apparatus including a manifold, according to one or more embodiments shown and described herein.

FIG. 6 illustrates a schematic view of a 12 layer (single cell culture module) cell culture apparatus 70 with a manifold assembly 72 including a module adapter 74. In embodiments, the unitary manifold adapter described above may be omitted.

Referring to FIG. 7, multiple of the cell culture apparatuses 10 are illustrated during a filling operation. In this example, the cell culture apparatuses 10 are all connected at the column structures 32 to a common fluid inlet line 76 for filling in parallel. The column structures 32' are connected to a filter 75 FIG. 8 illustrates multiple cell culture apparatuses 10 connected to each other using both the manifolds 20 and 22 for filling in series. As can be seen, a filling operation can be accomplished without any need for turning the cell culture apparatus 10 on its side and then turning the cell culture apparatus 10 upright, which can be heavy. Or, in embodiments, as shown for example in FIG. 19, the device can be turned on its side for filling, or elevated at a corner for filling.

Figure 9:
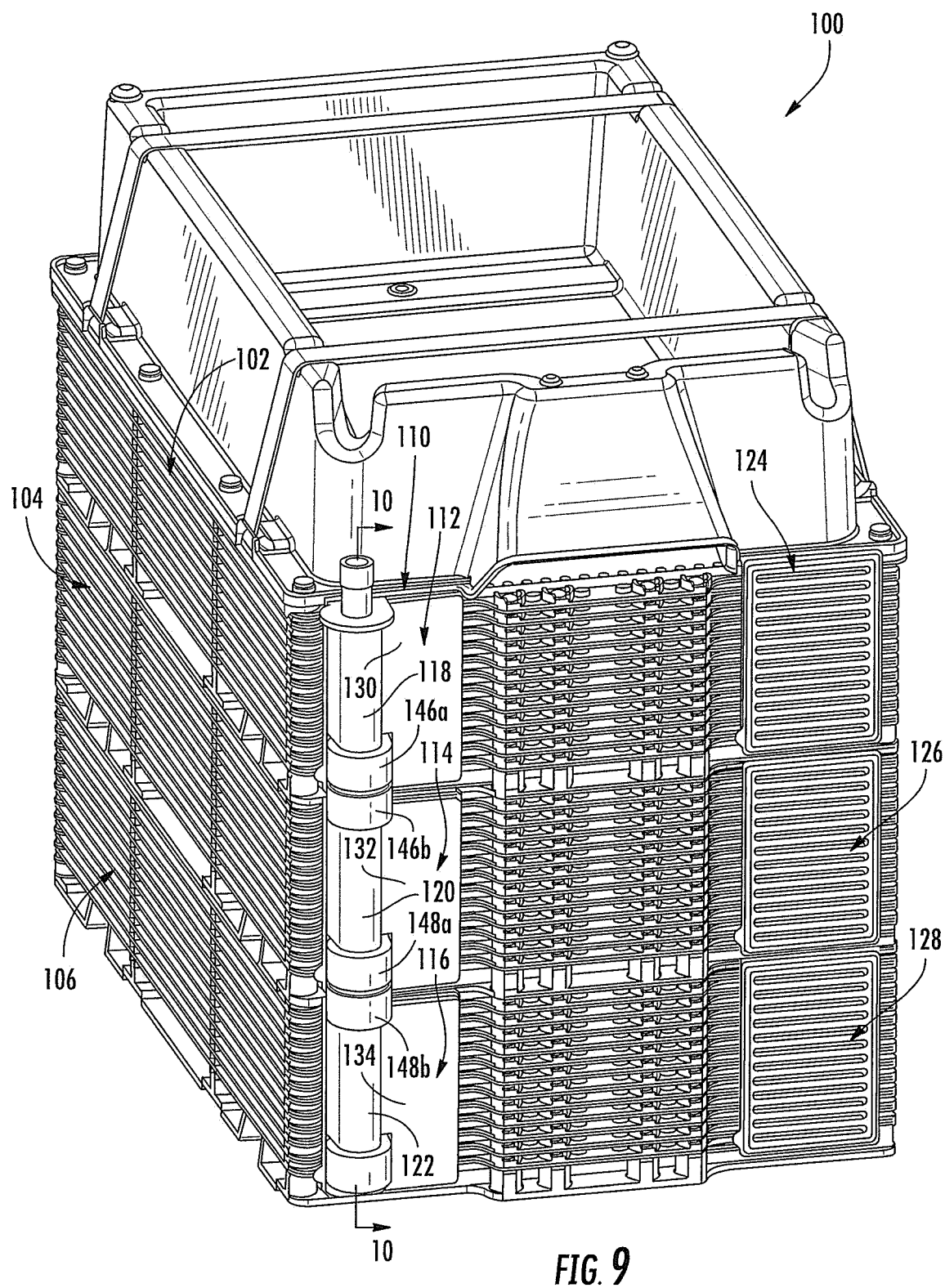
FIG. 9 illustrates another embodiment of a cell culture apparatus including manifolds, according to one or more embodiments shown and described herein.

Referring to FIG. 9, another embodiment of a cell culture apparatus 100 includes three cell culture modules 102, 104 and 106, each containing multiple layers of cell culture chambers 108, as described above. In this embodiment, the cell culture modules 102, 104 and 106 utilize a manifold 110 that is formed of multiple manifold segments 112, 114 and 116 that are connected together by column structure segments 118, 120 and 122 that are formed as monolithic parts of their respective manifold segments 112, 114 and 116. As can be seen, the other air flow manifold is removed from the cell culture apparatus 100 to expose module adapters 124, 126 and 128, which are similar or the same as those module adapters described above.

Figure 10:
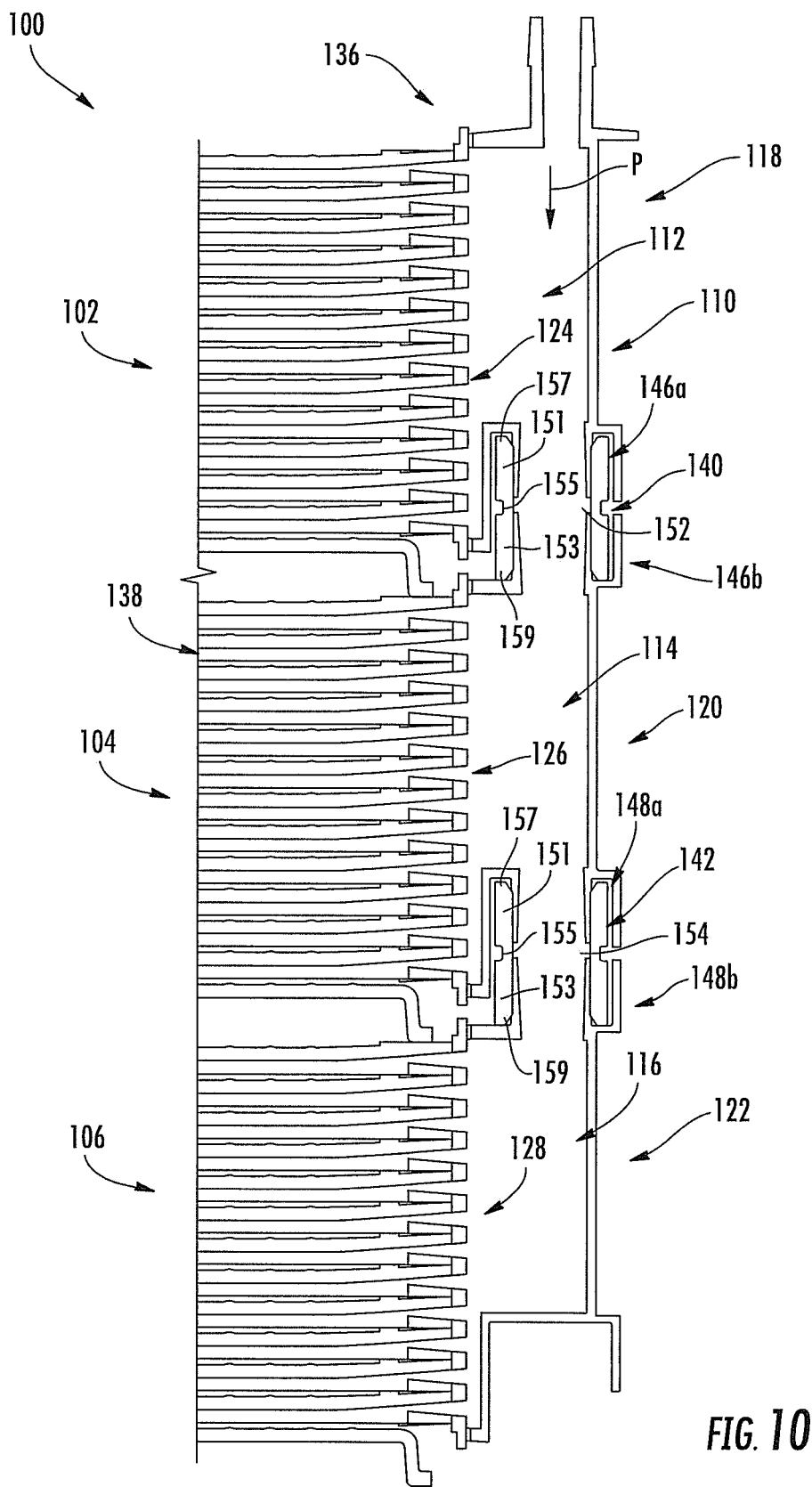
FIG. 10 illustrates a section view of the cell culture apparatus along lines 10-10 of FIG. 9, according to one or more embodiments shown and described herein.

Referring also to FIG. 10, a section view of the cell culture apparatus 100 and manifold segments 112, 114 and 116 are illustrated through line 10-10 of FIG. 9. The manifold 110 includes the manifold segments 112, 114 and 116, where each manifold segment 112, 114 and 116 is associated with a cell culture module 102, 104 and 106. The manifold segments 112, 114 and 116 each include a side wall base structure 130, 132 and 134 and a column structure segment 118, 120 and 122 that is formed monolithically with the respective side wall base structure 118, 120 and 122.

Referring particularly to FIG. 10, a section view of the cell culture apparatus 100 and manifold assembly 136 are illustrated through line 10-10 of FIG. 9. The manifold assembly 136 includes the manifold 110 that includes the manifold segments 112, 114 and 116, each including the column structure segment 118, 120 and 122. The column structure segments 118, 120 and 122 provide a fluid flow path P that leads to cell culture chambers 138 that are stacked one over the other, as described above. The module adapters 124, 126 and 128 are located behind the manifold segments 112, 114 and 116 and seal between the manifold segments 112, 114 and 116 and the cell culture modules 102, 104 and 106.

The column structure segments 118, 120 and 122 are interconnected using sealing rings 140 and 142. The sealing rings 140 and 142 may be received within shroud structures 146a, 146b and 148a, 148b and surround interfaces 152 and 154 between the column structure segments 118, 120 and 122. The sealing rings 140 and 142 may be formed of any material suitable for both connecting the column structure segments 118, 120 and 122 together, but also to provide a sealing function, such as plastics or rubber. The sealing rings 140 and 142 may be releasably used or permanently affixed between shroud structures 146 the column structure segments 118, 120 and 122 such as through welding, adhesives, overmolding, etc. Further, the sealing rings 140 and 142 may be formed of a relatively stiff or flexible materials, or combinations thereof. The sealing rings 140, 142 may be formed of an elastomer and include thicker portions 151 and 153 that optionally are separated by a relatively thinned portion 155 (e.g., a notch) that defines an area of increased flexibility that can facilitate sealing against the column structure segments 118, 120 and 122 at the interfaces 152. The thicker portions 151 and 153 have a lead in taper at both ends 157 and 159 to enable for ease of assembly.

Figure 10A:
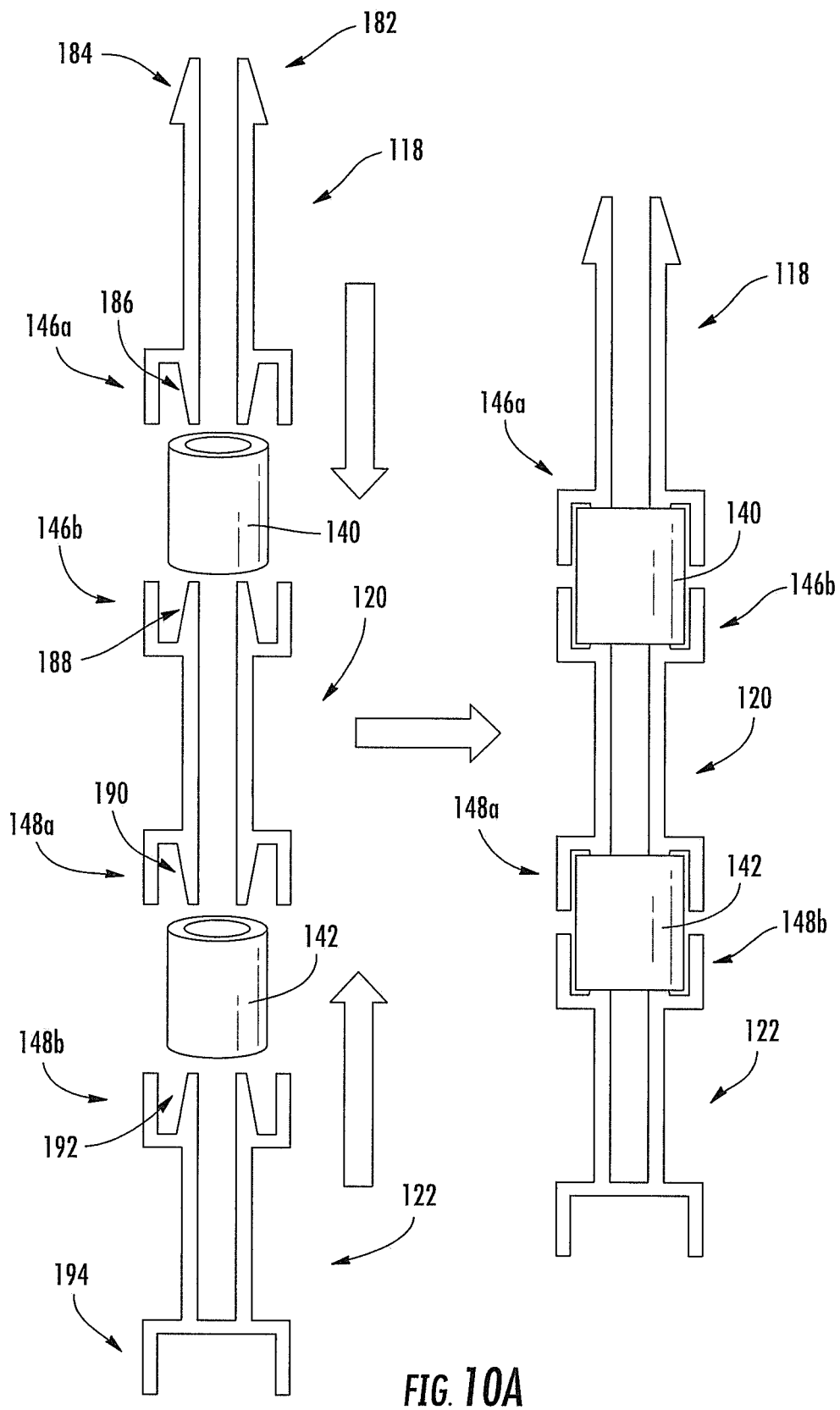
FIG. 10A illustrates a method of assembling the manifold of the cell culture apparatus of FIG. 9, according to one or more embodiments shown and described herein.

FIG. 10A illustrates a method of assembling the column structure segments 118, 120 and 122 together with the sealing rings 140 and 142. The column structure segment 118 is an upper column structure segment that includes an upper end 182 that can be formed as a barb structure 184 and a lower end 186 that is received within the sealing ring 140. In some embodiments, the lower end 186 tapers in wall thickness to facilitate insertion of the lower end 186 into the sealing ring 140. The column structure segment 120 is an intermediate column structure segment that includes an upper end 188 that is received within the sealing ring 140 and a lower end 190 that is received within the sealing ring 142. The lower end 190 and the upper end 188 may taper in wall thickness to facilitate insertion of the upper end 188 into the sealing ring 140 and the lower end 190 into the sealing ring 142. The column structure segment 122 is a lower column structure segment that includes an upper end 192 that is received within the sealing ring 142 and a lower end 194 that is closed to prevent passage of fluid therethrough. The upper end 192 may taper in wall thickness to facilitate insertion of the upper end 192 into the sealing ring 142.

Each column structure segment 118, 120 and 122 includes the shroud structure 146a, 146b, 148a, 148b. As assembled, adjacent shroud structures 146a, 146b and 148a and 148b face one another forming a partial enclosure that extends about the entire periphery of the sealing rings 140 and 142. This partial enclosure that is formed by the adjacent shroud structures 146 can protect the sealing rings 140 from contact and maintain seal integrity.

In embodiments, the modular cell culture device may be assembled by stacking one cell culture module on another cell culture module, each cell culture modules comprising multiple cell culture chambers; and connecting the cell culture chambers using a manifold, the manifold comprising a side wall base structure and a column that is formed as a monolithic part of the side wall base structure, the column structure defining an enlarged fluid flow pathway through the manifold and to the cell culture chambers to allow filling and emptying of the cell culture chambers of liquid medium.

Figure 11:
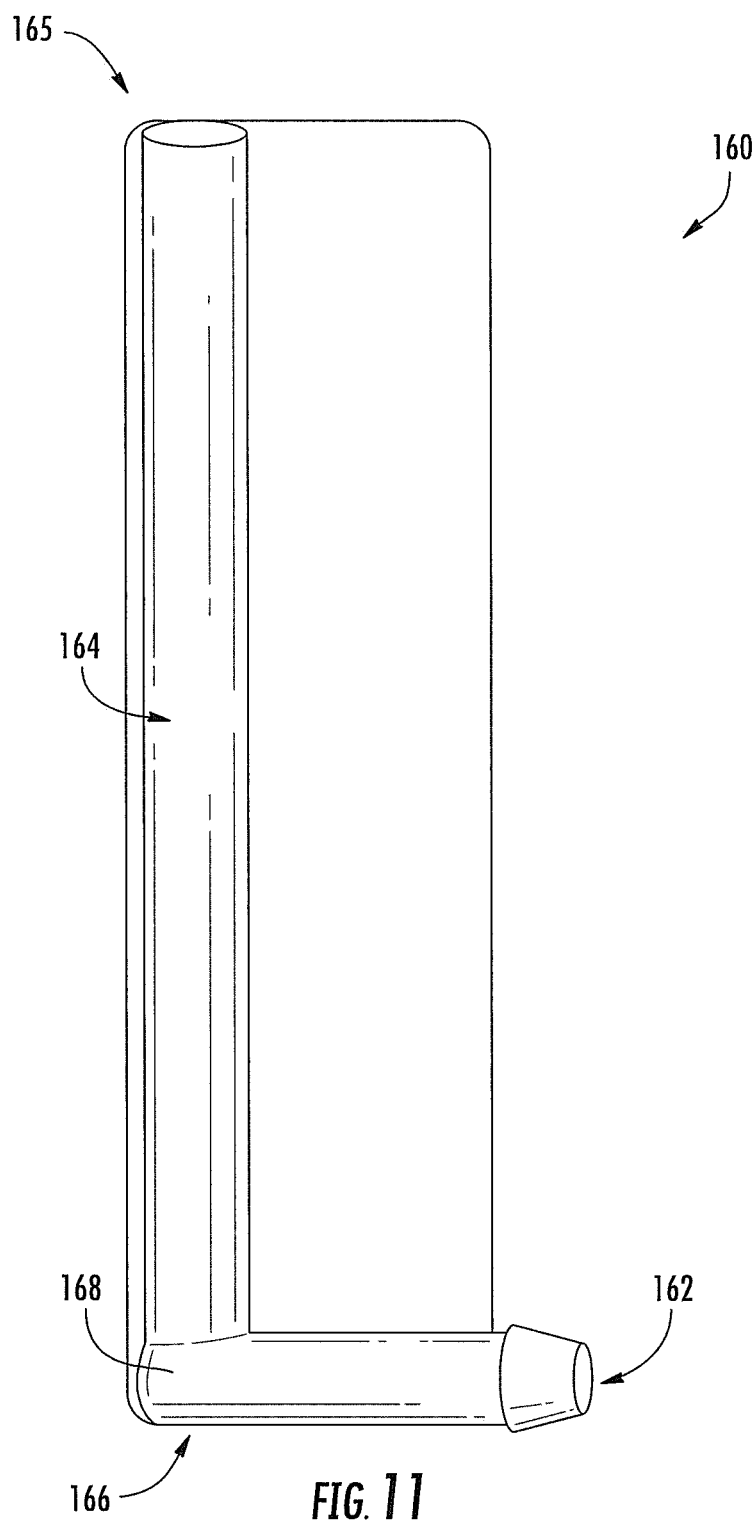
FIG. 11 is a schematic view of another embodiment of a manifold for use with a cell culture apparatus, according to one or more embodiments shown and described herein.

Referring to FIG. 11, another embodiment of a manifold 160 is illustrated for use with a manifold assembly 165 that is similar to the manifold of FIG. 3c. In this embodiment, an inlet opening 162 of column structure 164 that is a monolithic part of the manifold 160 is located at a bottom 166 of the manifold 160, as opposed to the top. The column structure 164 may include a bend 168 to that the inlet opening 162 faces outward to facilitate filling and emptying operations.

FIGS. 12 and 13 illustrate parallel and series filling, respectively, of multiple cell culture apparatuses 165 using the manifold of FIG. 11. Filling may occur when the devices are upright, as shown in FIG. 12, or on their sides, as shown, for example, in FIG. 19.

Figure 14:
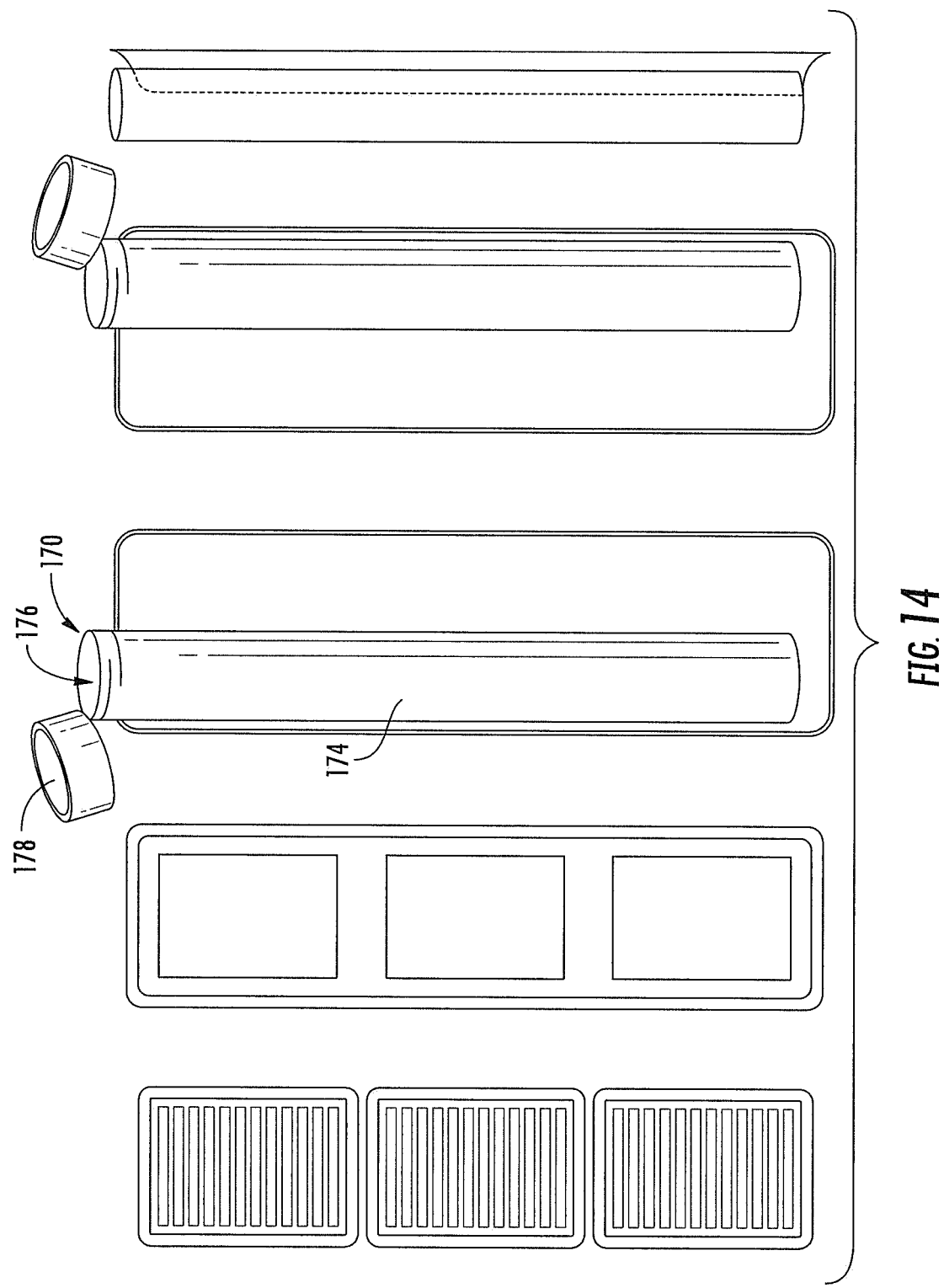
FIG. 14 illustrates another embodiment of a manifold for use with a cell culture apparatus, according to one or more embodiments shown and described herein.

Referring to FIG. 14, another embodiment of a manifold 170 for use with a manifold assembly 172 includes a column structure 174 that is a monolithic part of the manifold 170. In this embodiment, the column structure 174 has an inlet opening 176 that is openable and closable using a closing structure 178, such as a cap. Such a column structure arrangement can provide an open system where the cell culture apparatus can be filled by pouring fluid into the column structure 174. The manifold can be used for one or multiple cell culture modules.

Figure 15:
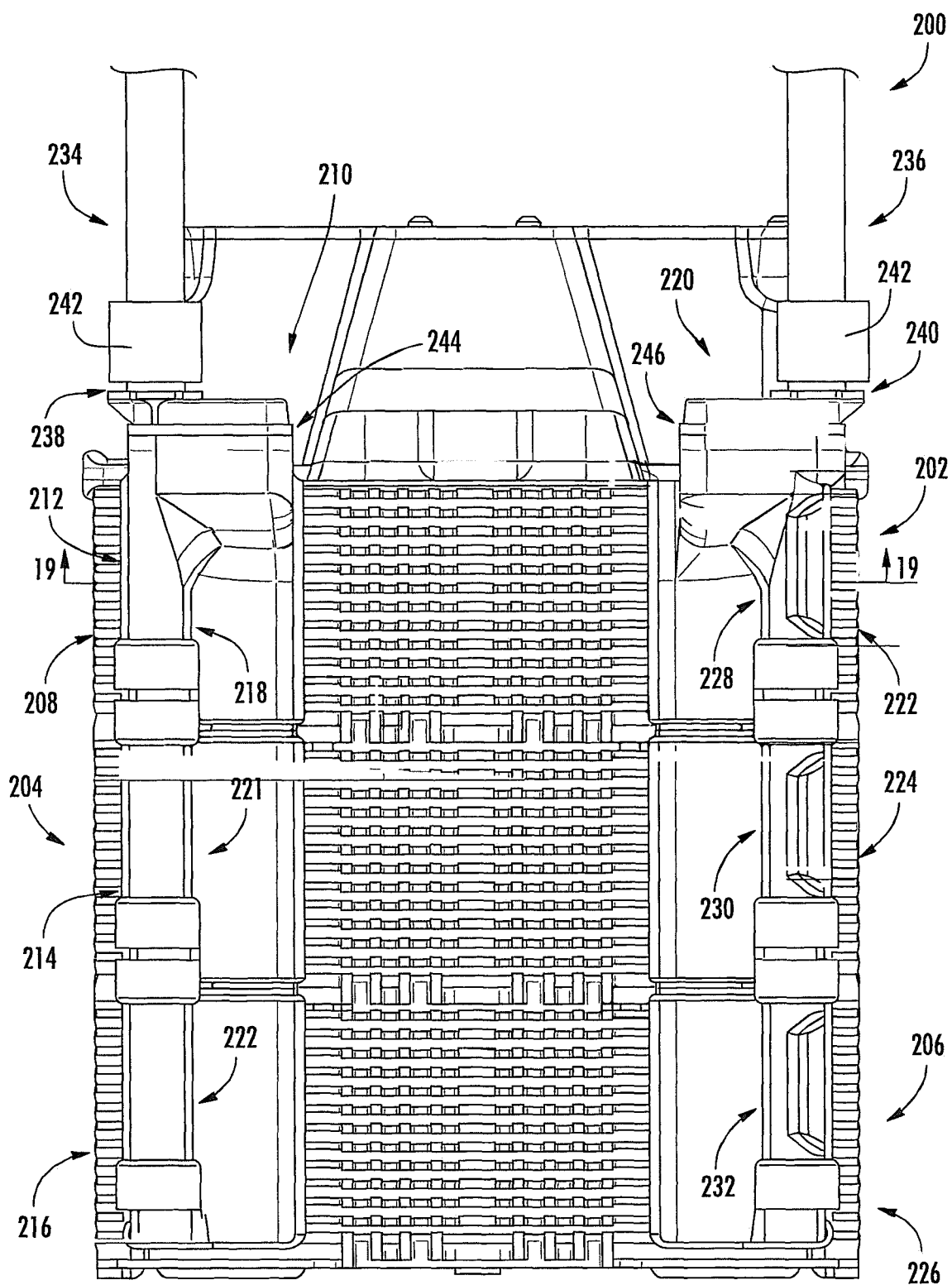
FIG. 15 illustrates a front view of another embodiment of a cell culture apparatus, according to one or more embodiments shown and described herein.
Figure 16:
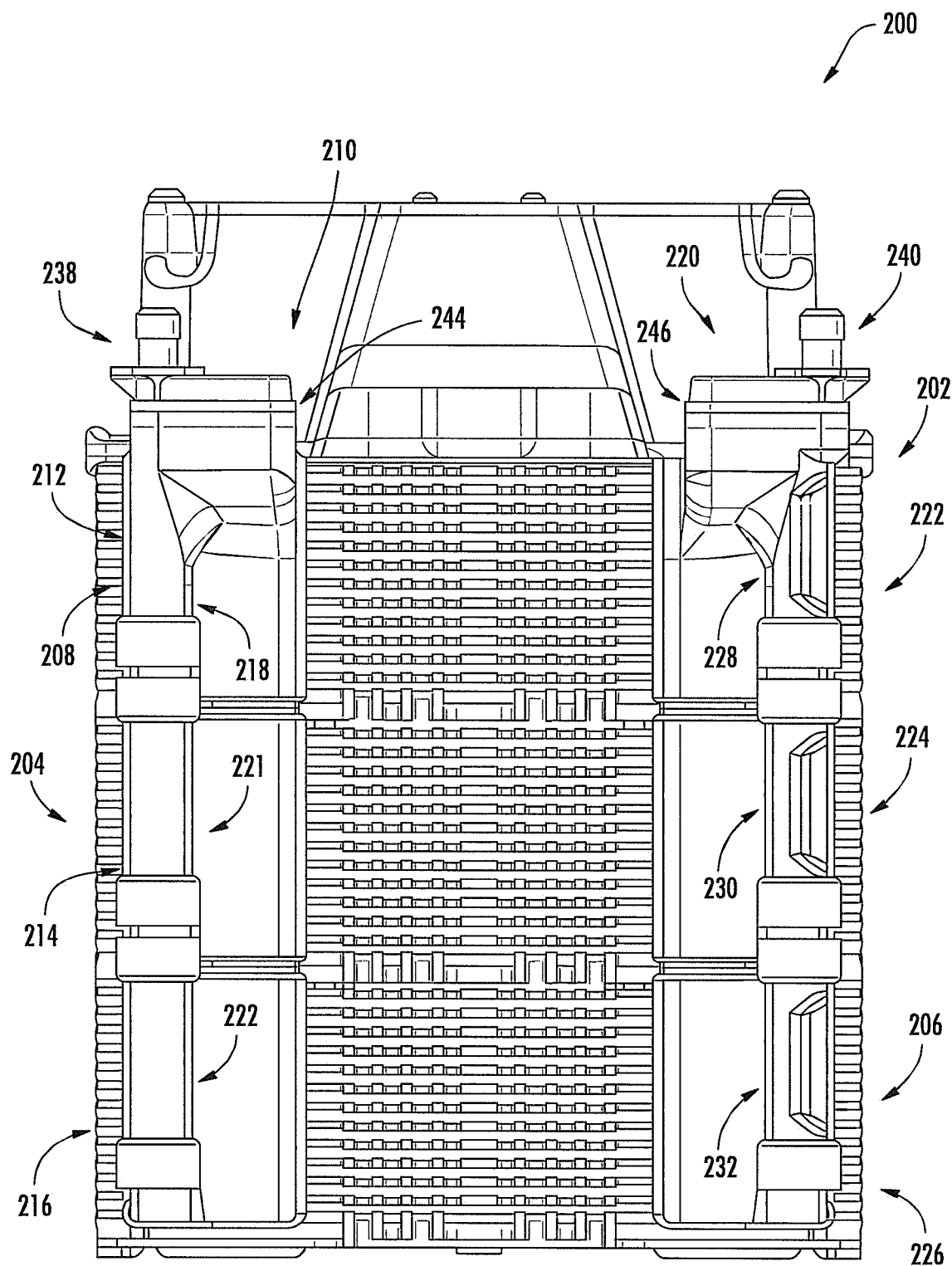
FIG. 16 illustrates another front view of the cell culture apparatus of FIG. 15.
Figure 17:
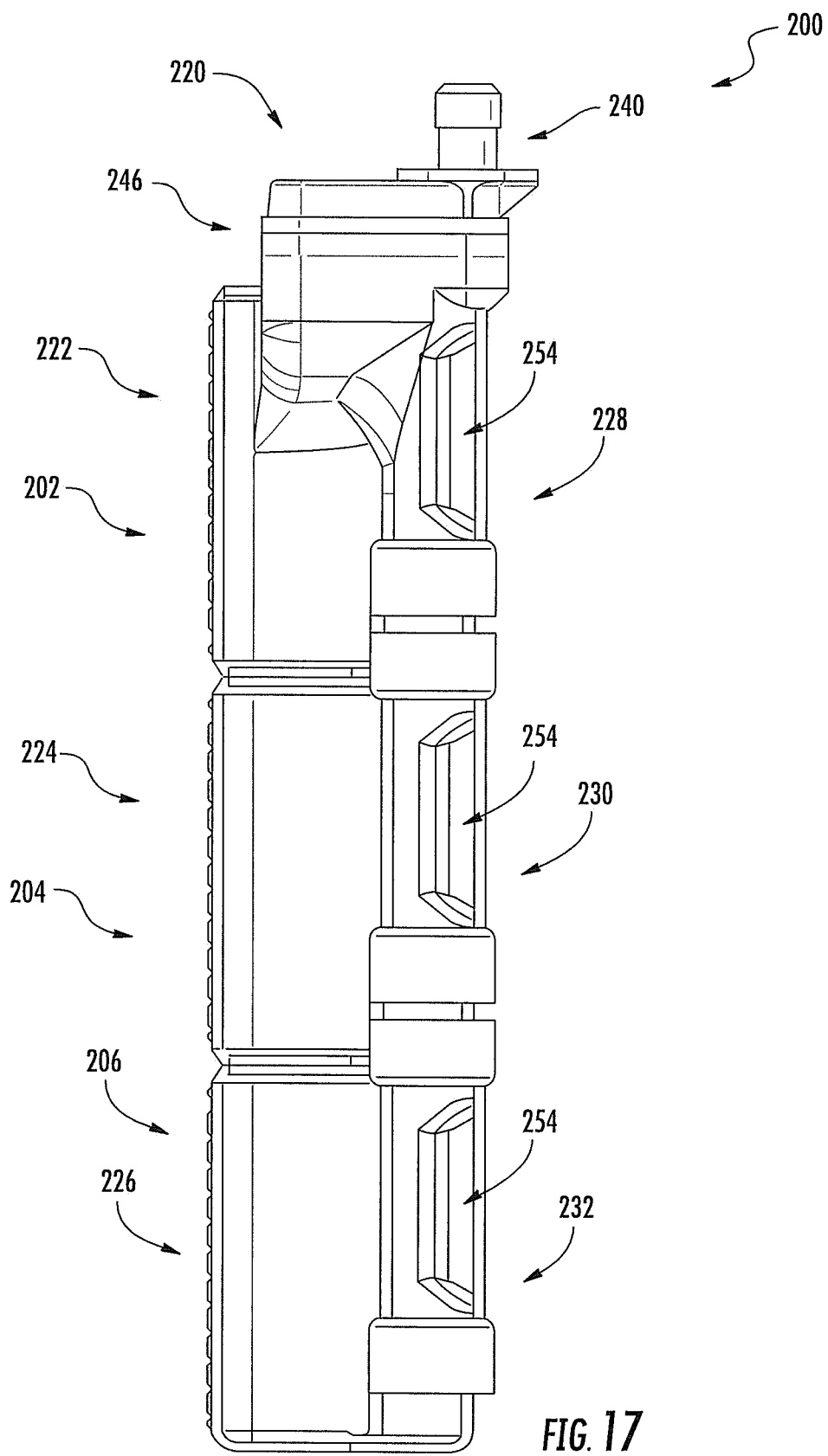
FIG. 17 illustrates a side view of the cell culture apparatus of FIG. 16.

Referring to FIGS. 15-17, another embodiment of a cell culture apparatus 200 includes many of the features provided by the cell culture apparatus 100 of FIG. 9 including three cell culture modules 202, 204 and 206, each containing multiple layers of cell culture chambers 208. As with the cell culture apparatus of FIG. 9, the cell culture modules 202, 204 and 206 utilize a manifold 210 that is formed of multiple manifold segments 212, 214 and 216 that are connected together by column structure segments 218, 221 and 222 that are formed as monolithic parts of their respective manifold segments 212, 214 and 216. Another manifold 220 is an air flow manifold that is also formed of multiple manifold segments 222, 224 and 226 that are connected together by column structure segments 228, 230 and 232 that are formed as monolithic parts of their respective manifold segments 222, 224 and 226.

FIG. 15 illustrates inlet and outlet tubes 234 and 236 that are connected to barb structures 238 and 240 (FIG. 16) that provide fluid communication with the column structure segments 218, 221, 222 and 228, 230, 232, respectively. Each inlet and outlet tube 234 and 236 is connected to its respective barb structure 238 and 240 by a connector 242. The connectors 242 may have a locking connection with the barb structure 238 and 240 to inhibit unintended removal of the inlet and outlet tubes 234 and 236 from the barb structures 238 and 240 and also to promote a sealing engagement between the connectors 242 and the barb structures 238 and 240.

Figure 18:
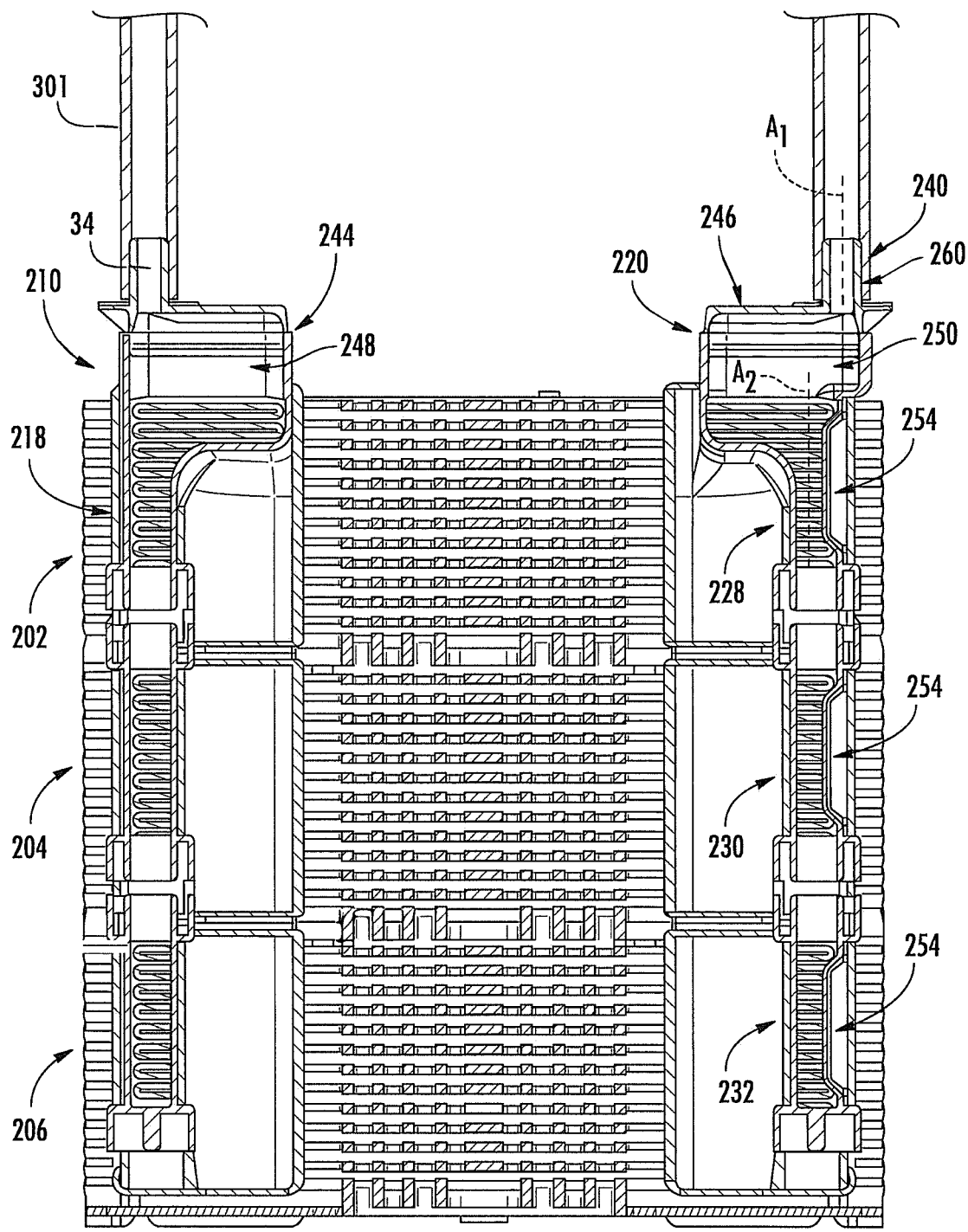
FIG. 18 illustrates a section view of the cell culture apparatus of FIG. 16.

Referring also to FIG. 18, the manifolds 210 and 220 are provided with risers 244 and 246 having internal volumes 248 and 250 that are in fluid communication with column structure segments 218 and 228. The risers 244 and 246 provide the internal volumes 248 and 250 located at least partially above the cell culture module 202 to provide a holding location for liquid and/or air during a filling operation. The riser 246, in particular, provides the internal volume 250 that is sized to allow air to escape the column structure segments 228, 230 and 232 during the filling operation, which facilitates filling of the cell culture modules 202, 204 and 206 and reduces pockets of air from being trapped within the manifolds 210 and 220. Providing the riser 246 and internal volume 250 can also allow for a reduction in volume of the column structure segments 228, 230 and 232, which can also facilitate evacuation of air during the filling operation and reduce pockets of air from being trapped within the manifolds 210 and 220.

In particular, each column structure segment 228, 230 and 232 includes an indent structure 254 that provides each column structure segment 228, 230 and 232 with a necked-down region providing a reduced volume compared to the absence of the indent structures 254. The indent structures 254 also provide the column structure segments 228, 230 and 232 with volumes that are different than the volumes of the column structure segments 218, 220 and 222, thereby providing an asymmetric column structure volume arrangement between column structures 250 and 252. In some embodiments, the internal volume 250 of the riser 246 may be selected based on the volume reduction provided by the indent structures 254. In some embodiments, the internal volume 250 of the riser 246 may be at least 50 percent of the volume reduction provided by the indent structures 254, such as at least 75 percent, such as at least 100 percent or more.

Referring particularly to FIG. 18, another difference between the cell culture apparatus 200 and the cell culture apparatus 100 of FIG. 9 is that the barb structure 240 provides an air outlet 260 that is offset from the column structure 252. In particular, the air outlet 260 has a central axis $A_1$ that is offset laterally from a central axis $A_2$ of the column structure 252 provided by the column structure segments 228, 230 and 232. The offset arrangement of the air outlet 260 inhibits the flow of liquid medium into the air outlet 260, which can then reach an air filter connected to the air outlet 260.

Figure 19:
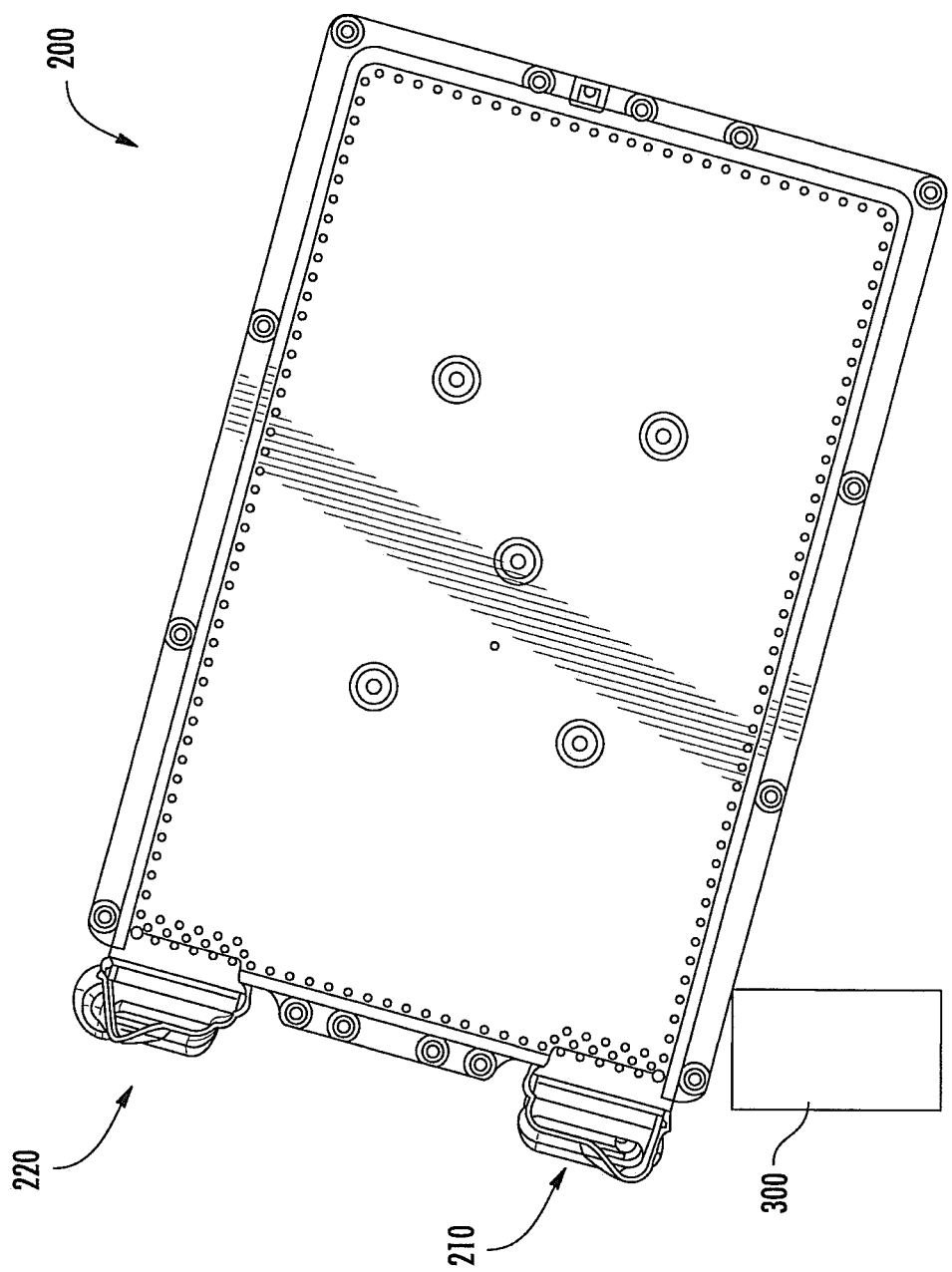
FIG. 19 is a section view of the cell culture apparatus of FIG. 15 along lines 19-19 illustrating a fill process, according to one or more embodiments shown and described herein.

Referring to FIG. 19, during a fill operation, the cell culture apparatus 200 may be tilted and supported on a spacer block 300. The cell culture apparatus 200 is then filled through the manifold 210 and air is evacuated through the manifold 220.

Figure 20A:
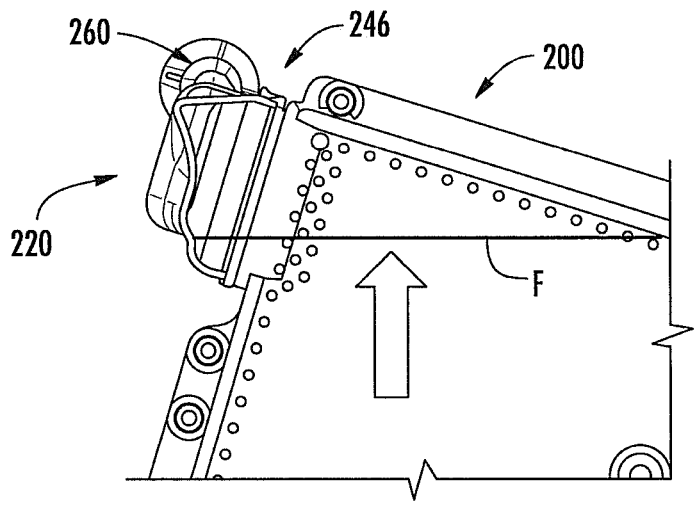
FIG. 20A is the section view of FIG. 19 illustrating a fill line.
Figure 20B:
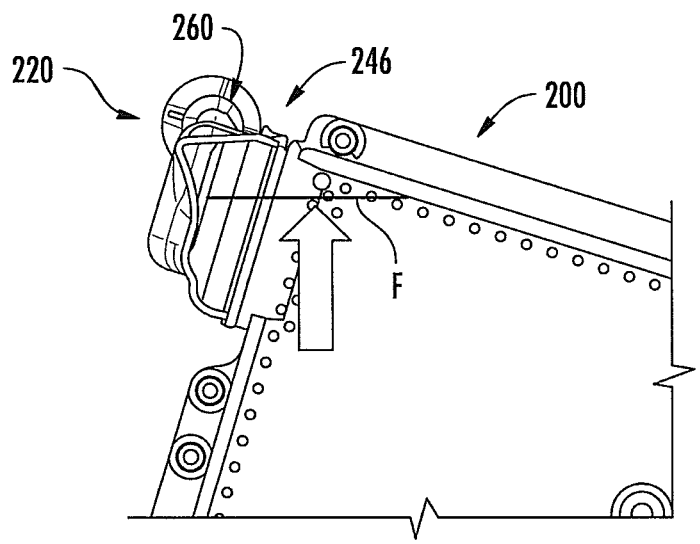
FIG. 20B is the section view of FIG. 19 illustrating the fill line progression.
Figure 20C:
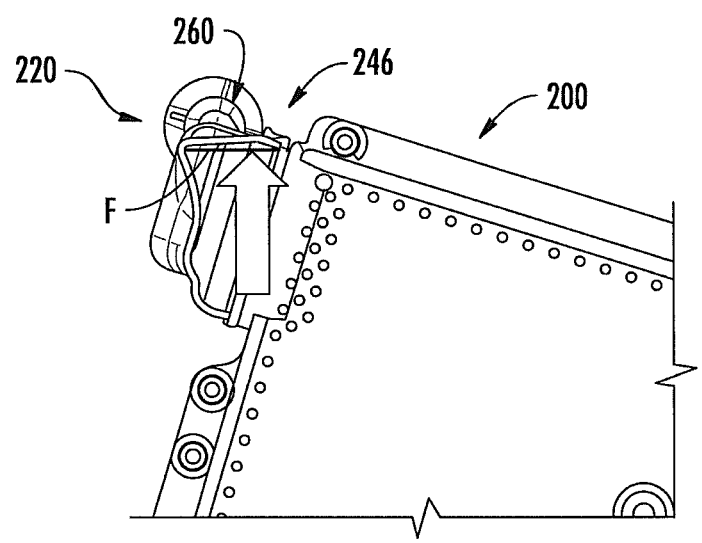
FIG. 20C is the section view of FIG. 19 illustrating the fill line progression.

FIGS. 20A-20C illustrate the filling progression approaching the end of the filling process showing fill line F. The shapes of the indent structures 154 and/or the riser 246 can be selected to reduce or even eliminate air pockets within the manifold 220 once the entire cell culture apparatus 200 is filled. As can be seen by FIG. 20C, the shape of the indent structure 154 may be selected to provide a wall that is shaped to be flush with the fill line F with the cell culture apparatus 200 tilted to a predetermined angle provided by the spacer block 300. Additionally, the offset arrangement of the air outlet 260 allows for complete filling of the manifold 220 with medium while reducing flow of liquid medium into the air outlet 260 as the air outlet is out of alignment with the column structure 252. In addition, this angle of the indent structures 154 and/or the riser 246 allows for as nearly complete filling as possible, without over-filling. Over-filling of the device may cause media to spill out of the device as the device is manipulated and may cause contamination. For example, often a vent filter is present in the tubing 301 which extends from the device (see, for example, FIG. 18). If the vent filter is wetted with protein-rich media, the vent filter may become clogged. A clogged vent filter may prevent the system from properly filling or emptying because the flow path is blocked. This may create a contamination risk if a user removes the vent filter either to wash it or to allow the device to flow. Therefore, providing the indent structure 154 and the riser angles allows for more complete filling of the device without over-filling which can result in contamination or obstruction of the fluid flow path.

Manifolds, or portions thereof, as described herein may be formed from any suitable material. For example, a manifold, or component thereof may be formed from a biocompatible polymeric material. In various embodiments, a manifold is formed from one or more materials from which a cell culture module is formed.

It will be understood that a manifold or cell culture module may be of any suitable size. In many of the depicted embodiments, the column structures or components thereof are depicted as having a rounded cross-sectional shape, but it will be understood that they may have any suitable cross-sectional shape, such as rectangular, ellipsoidal or the like. It will be further understood that a cell culture module may include any number of cell culture chambers. In some embodiments, a cell culture module has, for example, 10 stacked cell culture chambers or 12 stacked cell culture chambers. Multiple ones of the cell culture modules may be stacked, one on the other, to form a cell culture apparatus. In embodiments, any number of stacked cell culture chambers may be assembled in cell culture modules, providing manifolds with any number of cell culture chambers.

Thus, embodiments of CELL CULTURE APPARATUSES WITH MANIFOLDS INCLUDING COLUMN STRUCTURES are disclosed. One skilled in the art will appreciate that the cell culture apparatuses and methods described herein can be practiced with embodiments other than those disclosed. The disclosed embodiments are presented for purposes of illustration and not limitation.

The invention claimed is:

1. A cell culture apparatus, comprising:
a cell culture module comprising multiple cell culture chambers;
each cell culture chamber having a top, a bottom and sidewalls, defining an interior space for culturing cells;
wherein each cell culture chamber has at least one inlet in a sidewall of the cell culture chamber through which liquid can flow into and out of the cell culture chamber;
wherein the multiple cell culture chambers are stacked one above the other to form the cell culture module;
a manifold comprising a side wall base structure and a monolithic column;
wherein the manifold is aligned along a side of the cell culture module;
wherein the manifold provides a fluid pathway from a manifold opening to each of the cell culture chambers through cell culture chamber inlets;
wherein the monolithic column is a portion of the manifold and comprises a cross-sectional shape extending along the multiple cell culture chambers;
and wherein the monolithic column provides an enlarged volume inside the manifold to enable fluid to flow through the manifold to the cell culture chamber inlets.

2. The cell culture apparatus of claim 1, wherein the manifold opening extends above the top-most stacked cell culture module.

3. The cell culture apparatus of claim 1, comprising multiple cell culture modules and the manifold comprises manifold segments where each manifold segment is associated with one of the cell culture modules.

4. The cell culture apparatus of claim 3, wherein each manifold segment comprises a side wall base structure segment and a column structure segment that is formed as a monolithic part of the side wall base structure segment.

5. The cell culture apparatus of claim 4, wherein the column structure segments of adjacent manifold segments are interconnected and in fluid communication.

6. The cell culture apparatus of claim 5, wherein the column structure segments of adjacent manifold segments are interconnected by a sealing ring.

7. The cell culture apparatus of claim 6, wherein the sealing ring seals an interface between the column structure segments of adjacent manifold segments.

8. The cell culture apparatus of claim 6, wherein the sealing ring comprises relatively thick portions that are separated by a relatively thin portion in the form of a notch that defines an area of increased flexibility compared to the thick portions.

9. The cell culture apparatus of claim 6, wherein each column structure segment comprises a shroud structure, wherein adjacent shroud structures face each other thereby forming a partial enclosure that extends about an entire periphery of the sealing ring.

* * * * *